(12) United States Patent
Cooper et al.

(10) Patent No.: US 12,090,036 B2
(45) Date of Patent: Sep. 17, 2024

(54) STORAGE ASSEMBLY FOR PROSTHETIC VALVE

(71) Applicant: Edwards Lifesciences Corporation, Irvine, CA (US)

(72) Inventors: Alexander H. Cooper, Costa Mesa, CA (US); Michael R. Bialas, Lake Forest, CA (US); David M. Taylor, Lake Forest, CA (US); Gregory Scott Tyler, II, Winston-Salem, NC (US); Zachary R. Kowalski, Irvine, CA (US); Art Z. Kwan, Irvine, CA (US); Darshin S. Patel, San Juan Capistrano, CA (US); Asher L. Metchik, Rolling Hills Estates, CA (US); Michael J. Popp, Irvine, CA (US); Amanda Kristine Anderson White, Mountain View, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 133 days.

(21) Appl. No.: 17/654,512

(22) Filed: Mar. 11, 2022

(65) Prior Publication Data
US 2022/0296352 A1    Sep. 22, 2022

Related U.S. Application Data

(63) Continuation of application No. 16/447,530, filed on Jun. 20, 2019, now Pat. No. 11,273,024, which is a
(Continued)

(51) Int. Cl.
A61F 2/24    (2006.01)
A61F 2/00    (2006.01)
A61F 2/95    (2013.01)

(52) U.S. Cl.
CPC .......... *A61F 2/0095* (2013.01); *A61F 2/2415* (2013.01); *A61F 2/2418* (2013.01);
(Continued)

(58) Field of Classification Search
CPC .... A61F 2/2418; A61F 2/2433; A61F 2/2436; A61F 2/2439; A61F 2/0095; A61F 2/2427; A61F 2/243
See application file for complete search history.

(56) References Cited

U.S. PATENT DOCUMENTS 4,011,947 A    3/1977 Sawyer
4,012,472 A    3/1977 Lindsey
(Continued)

FOREIGN PATENT DOCUMENTS

CA    2767527 A1    1/2011
DE    19532846 A1    3/1997
(Continued)

*Primary Examiner* — Tuan V Nguyen
(74) *Attorney, Agent, or Firm* — Ryan A. Heck; Klarquist Sparkman LLP

(57) ABSTRACT

In a particular embodiment, the present disclosure provides a prosthetic valve delivery assembly that includes a storage tube and a nose cone cap. A prosthetic valve having a frame is at least partially disposed within the storage tube. A nose cone is disposed about an elongated shaft. The nose cone cap and the storage tube have mating first and second locking member that can be coupled to selectively secure the nose cone cap to the storage tube.

20 Claims, 22 Drawing Sheets

Related U.S. Application Data continuation of application No. 15/364,670, filed on Nov. 30, 2016, now Pat. No. 10,357,351.

(60) Provisional application No. 62/263,540, filed on Dec. 4, 2015.

(52) U.S. Cl.
CPC .......... *A61F 2/2433* (2013.01); *A61F 2/2436* (2013.01); *A61F 2/2439* (2013.01); *A61F 2/2412* (2013.01); *A61F 2/9517* (2020.05)

(56) References Cited

U.S. PATENT DOCUMENTS

| | | | |
|---|---|---|---|
| 4,035,849 A | 7/1977 | Angell et al. |
| 4,101,031 A | 7/1978 | Cromie |
| 4,182,446 A | 1/1980 | Penny |
| 4,211,325 A | 7/1980 | Wright |
| 4,216,860 A | 8/1980 | Heimann |
| 4,592,340 A | 6/1986 | Boyles |
| 4,697,703 A | 10/1987 | Will |
| 4,779,727 A | 10/1988 | Taterka et al. |
| 4,801,015 A | 1/1989 | Lubock et al. |
| 4,994,077 A | 2/1991 | Dobben |
| 5,059,177 A | 10/1991 | Towne et al. |
| 5,098,391 A | 3/1992 | Pantages et al. |
| 5,167,223 A | 12/1992 | Koros et al. |
| 5,236,450 A | 8/1993 | Scott |
| 5,336,616 A | 8/1994 | Livesey et al. |
| 5,392,918 A | 2/1995 | Harrison |
| 5,411,552 A | 5/1995 | Andersen et al. |
| 5,480,425 A | 1/1996 | Ogilive |
| 5,531,785 A | 7/1996 | Love et al. |
| 5,554,185 A | 9/1996 | Block et al. |
| 5,560,487 A | 10/1996 | Starr |
| 5,578,076 A | 11/1996 | Krueger et al. |
| 5,582,607 A | 12/1996 | Lackman |
| 5,591,195 A | 1/1997 | Taheri et al. |
| 5,599,305 A | 2/1997 | Hermann et al. |
| 5,615,770 A | 4/1997 | Applebaum et al. |
| 5,639,274 A | 6/1997 | Fischell et al. |
| 5,690,226 A | 11/1997 | N'Guyen |
| 5,720,391 A | 2/1998 | Dohm et al. |
| 5,728,068 A | 3/1998 | Leone et al. |
| 5,776,187 A | 7/1998 | Krueger et al. |
| 5,800,531 A | 9/1998 | Cosgrove et al. |
| 5,823,342 A | 10/1998 | Caudillo et al. |
| 5,840,081 A | 11/1998 | Andersen et al. |
| 5,848,691 A | 12/1998 | Morris et al. |
| 5,868,253 A | 2/1999 | Krueger et al. |
| 5,947,284 A | 9/1999 | Foster |
| 5,968,068 A | 10/1999 | Dehdashtian et al. |
| 5,980,569 A | 11/1999 | Scirica |
| 5,984,959 A | 11/1999 | Robertson et al. |
| 6,040,416 A | 3/2000 | Sekharipuram et al. |
| 6,068,121 A | 5/2000 | McGlinch |
| 6,090,138 A | 7/2000 | Chasak et al. |
| 6,126,007 A | 10/2000 | Kari et al. |
| 6,168,614 B1 | 1/2001 | Andersen et al. |
| 6,197,053 B1 | 3/2001 | Cosgrove et al. |
| 6,199,696 B1 | 3/2001 | Lytle et al. |
| 6,217,585 B1 | 4/2001 | Houser et al. |
| 6,346,094 B2 | 2/2002 | West et al. |
| 6,379,372 B1 | 4/2002 | Dehdashtian et al. |
| 6,416,547 B1 | 7/2002 | Erickson et al. |
| 6,454,799 B1 | 9/2002 | Schreck |
| 6,458,153 B1 | 10/2002 | Bailey et al. |
| 6,461,382 B1 | 10/2002 | Cao |
| 6,527,979 B2 | 3/2003 | Constantz et al. |
| 6,534,004 B2 | 3/2003 | Chen et al. |
| 6,582,462 B1 | 6/2003 | Andersen et al. |
| 6,591,998 B2 | 7/2003 | Haynes et al. |
| D480,816 S | 10/2003 | McMichael et al. |
| 6,652,578 B2 | 11/2003 | Bailey et al. |
| 6,723,122 B2 | 4/2004 | Yang et al. |
| 6,730,118 B2 | 5/2004 | Spenser et al. |
| 6,733,525 B2 | 5/2004 | Yang et al. |
| 6,736,845 B2 | 5/2004 | Marquez et al. |
| 6,767,362 B2 | 7/2004 | Schreck |
| 6,830,584 B1 | 12/2004 | Seguin |
| 6,893,460 B2 | 5/2005 | Spenser et al. |
| 6,908,481 B2 | 6/2005 | Cribier |
| 6,966,925 B2 | 11/2005 | Stoble |
| 7,000,770 B2 | 2/2006 | Clarke et al. |
| 7,018,406 B2 | 3/2006 | Seguin et al. |
| 7,018,408 B2 | 3/2006 | Bailey et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,389,874 B2 | 6/2008 | Quest et al. |
| 7,393,360 B2 | 7/2008 | Spenser et al. |
| 7,510,575 B2 | 3/2009 | Spenser et al. |
| 7,549,270 B2 | 6/2009 | Rowe et al. |
| 7,585,321 B2 | 9/2009 | Cribler |
| 7,618,446 B2 | 11/2009 | Andersen et al. |
| 7,699,168 B2 | 4/2010 | Ryan et al. |
| 7,712,606 B2 | 5/2010 | Salahieh et al. |
| 7,749,266 B2 | 7/2010 | Forster et al. |
| 7,780,726 B2 | 8/2010 | Seguin |
| 7,785,366 B2 | 8/2010 | Maurer et al. |
| 7,866,468 B2 | 1/2011 | Kyritsis |
| 7,967,138 B2 | 6/2011 | Ryan et al. |
| 7,993,394 B2 | 8/2011 | Hariton et al. |
| 8,029,556 B2 | 10/2011 | Rowe |
| 8,167,932 B2 | 5/2012 | Bourang et al. |
| 8,182,530 B2 | 5/2012 | Huber |
| 8,449,606 B2 | 5/2013 | Ellasen et al. |
| 8,584,849 B2 | 11/2013 | McCaffrey |
| 8,652,145 B2 | 2/2014 | Maimon et al. |
| 8,652,202 B2 | 2/2014 | Alon et al. |
| 8,652,203 B2 | 2/2014 | Quadri et al. |
| 8,801,776 B2 | 8/2014 | House et al. |
| 9,155,619 B2 | 10/2015 | Liu et al. |
| 9,168,131 B2 | 10/2015 | Yohanan et al. |
| 9,867,700 B2 | 1/2018 | Bakis et al. |
| 2002/0032481 A1 | 3/2002 | Gabbay |
| 2002/0120328 A1 | 8/2002 | Pathak et al. |
| 2002/0151970 A1 | 10/2002 | Garrison et al. |
| 2002/0161377 A1 | 10/2002 | Rabkin |
| 2003/0040792 A1 | 2/2003 | Gabbay |
| 2003/0050694 A1 | 3/2003 | Yang et al. |
| 2003/0070944 A1 | 4/2003 | Nigam |
| 2003/0213715 A1 | 11/2003 | Klepac et al. |
| 2004/0133263 A1 | 7/2004 | Dusbabek et al. |
| 2004/0186565 A1 | 9/2004 | Schreck |
| 2004/0210304 A1 | 10/2004 | Seguin et al. |
| 2004/0236411 A1 | 11/2004 | Sarac et al. |
| 2004/0243214 A1 | 12/2004 | Farrell et al. |
| 2004/0260389 A1 | 12/2004 | Case et al. |
| 2005/0075731 A1 | 4/2005 | Artof et al. |
| 2005/0096736 A1 | 5/2005 | Osse et al. |
| 2005/0113910 A1 | 5/2005 | Paniagua et al. |
| 2005/0137688 A1 | 6/2005 | Salahieh et al. |
| 2005/0137693 A1 | 6/2005 | Haug et al. |
| 2005/0137697 A1 | 6/2005 | Salahieh et al. |
| 2005/0149159 A1 | 7/2005 | Andreas et al. |
| 2005/0203614 A1 | 9/2005 | Forster et al. |
| 2005/0203617 A1 | 9/2005 | Forster et al. |
| 2005/0241981 A1 | 11/2005 | Gupta et al. |
| 2006/0025857 A1 | 2/2006 | Bergheim et al. |
| 2006/0149360 A1 | 7/2006 | Schwammenthal et al. |
| 2006/0155363 A1 | 7/2006 | LaDuca et al. |
| 2006/0195183 A1 | 8/2006 | Navia et al. |
| 2006/0259136 A1 | 11/2006 | Nguyen et al. |
| 2006/0276813 A1 | 12/2006 | Greenberg |
| 2006/0282045 A1 | 12/2006 | Wilkinson et al. |
| 2006/0287719 A1 | 12/2006 | Rowe et al. |
| 2007/0005131 A1 | 1/2007 | Taylor |
| 2007/0073389 A1 | 3/2007 | Bolduc et al. |
| 2007/0084144 A1 | 4/2007 | Labrecque et al. |
| 2007/0088431 A1 | 4/2007 | Bourang et al. |
| 2007/0203575 A1 | 8/2007 | Forster et al. |
| 2007/0213813 A1 | 9/2007 | Von Segesser et al. |

(56) References Cited

U.S. PATENT DOCUMENTS

| | | |
|---|---|---|
| 2007/0265700 A1 | 11/2007 | Eliasen et al. |
| 2008/0023346 A1 | 1/2008 | Vonderwalde |
| 2008/0058766 A1 | 3/2008 | Gilson et al. |
| 2008/0082163 A1 | 4/2008 | Woo |
| 2008/0125853 A1 | 5/2008 | Bailey et al. |
| 2008/0177381 A1 | 7/2008 | Navia et al. |
| 2008/0294230 A1 | 11/2008 | Parker |
| 2008/0319526 A1 | 12/2008 | Hill et al. |
| 2009/0099638 A1 | 4/2009 | Grewe |
| 2009/0130162 A2 | 5/2009 | Pathak et al. |
| 2009/0157175 A1 | 6/2009 | Benichou |
| 2009/0164005 A1 | 6/2009 | Dove et al. |
| 2009/0276040 A1 | 11/2009 | Rowe et al. |
| 2009/0281619 A1 | 11/2009 | Le et al. |
| 2009/0319037 A1 | 12/2009 | Rowe et al. |
| 2010/0049313 A1 | 2/2010 | Alon et al. |
| 2010/0191326 A1 | 7/2010 | Alkhatib |
| 2010/0198347 A1 | 8/2010 | Zakay et al. |
| 2010/0219092 A1 | 9/2010 | Salahieh et al. |
| 2011/0015729 A1 | 1/2011 | Jimenez et al. |
| 2011/0040374 A1 | 2/2011 | Goetz et al. |
| 2011/0147251 A1 | 6/2011 | Hodshon et al. |
| 2011/0301702 A1 | 12/2011 | Rust et al. |
| 2012/0071969 A1 | 3/2012 | Li et al. |
| 2012/0078353 A1 | 3/2012 | Quadri et al. |
| 2012/0103840 A1 | 5/2012 | McCaffrey |
| 2012/0123529 A1 | 5/2012 | Levi et al. |
| 2012/0158128 A1 | 6/2012 | Gautam et al. |
| 2012/0239142 A1* | 9/2012 | Liu .................. A61F 2/915 623/2.11 |
| 2012/0305441 A1 | 12/2012 | Murray et al. |
| 2013/0123914 A1 | 5/2013 | Fish et al. |
| 2013/0206634 A1 | 8/2013 | Tijssen |
| 2013/0317598 A1 | 11/2013 | Rowe et al. |
| 2013/0325111 A1 | 12/2013 | Campbell et al. |
| 2014/0202908 A1 | 7/2014 | Liburd et al. |
| 2014/0216955 A1 | 8/2014 | Murray et al. |
| 2014/0343670 A1 | 11/2014 | Bakis et al. |
| 2015/0094801 A1 | 4/2015 | Von Segesser et al. |
| 2015/0157455 A1 | 6/2015 | Hoang et al. |
| 2015/0238315 A1 | 8/2015 | Rabito et al. |
| 2015/0305867 A1 | 10/2015 | Liu et al. |
| 2017/0056149 A1 | 3/2017 | Rajpara et al. |
| 2017/0128197 A1 | 5/2017 | Bialas et al. |
| 2017/0156839 A1 | 6/2017 | Cooper et al. |
| 2017/0156859 A1 | 6/2017 | Chang et al. |
| 2017/0231765 A1 | 8/2017 | Desrosiers et al. |
| 2017/0258584 A1 | 9/2017 | Chang et al. |

FOREIGN PATENT DOCUMENTS

| | | |
|---|---|---|
| DE | 19907646 A1 | 8/2000 |
| EP | 0592410 B1 | 10/1995 |
| EP | 1796597 A2 | 6/2007 |
| EP | 2218403 A1 | 8/2010 |
| FR | 2815844 A1 | 5/2002 |
| WO | 9117720 A1 | 11/1991 |
| WO | 9829057 A1 | 7/1998 |
| WO | 9951167 A2 | 10/1999 |
| WO | 0041652 A1 | 7/2000 |
| WO | 0149213 A2 | 7/2001 |
| WO | 0154625 A1 | 8/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 03047468 A1 | 6/2003 |
| WO | 2005084595 A1 | 9/2005 |
| WO | 2006111391 A1 | 10/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2008035337 A2 | 3/2008 |
| WO | 2008124844 A1 | 10/2008 |
| WO | 2010121076 A2 | 10/2010 |
| WO | 2012150290 A1 | 11/2012 |

* cited by examiner

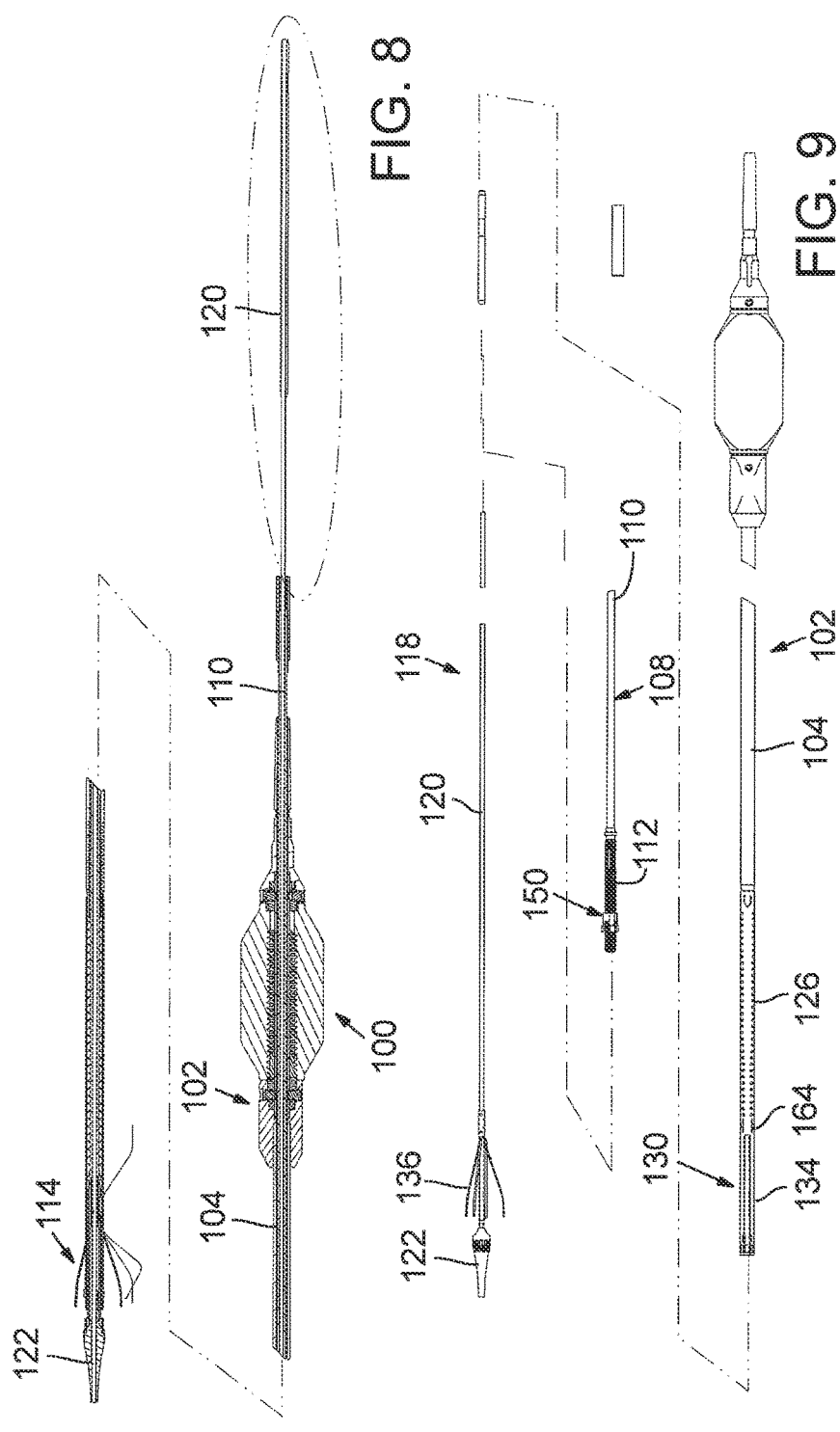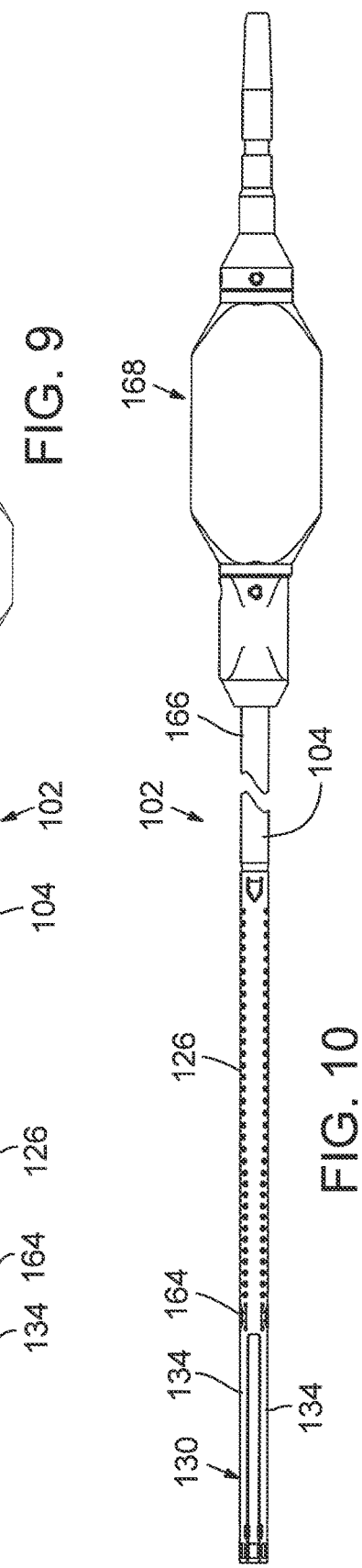

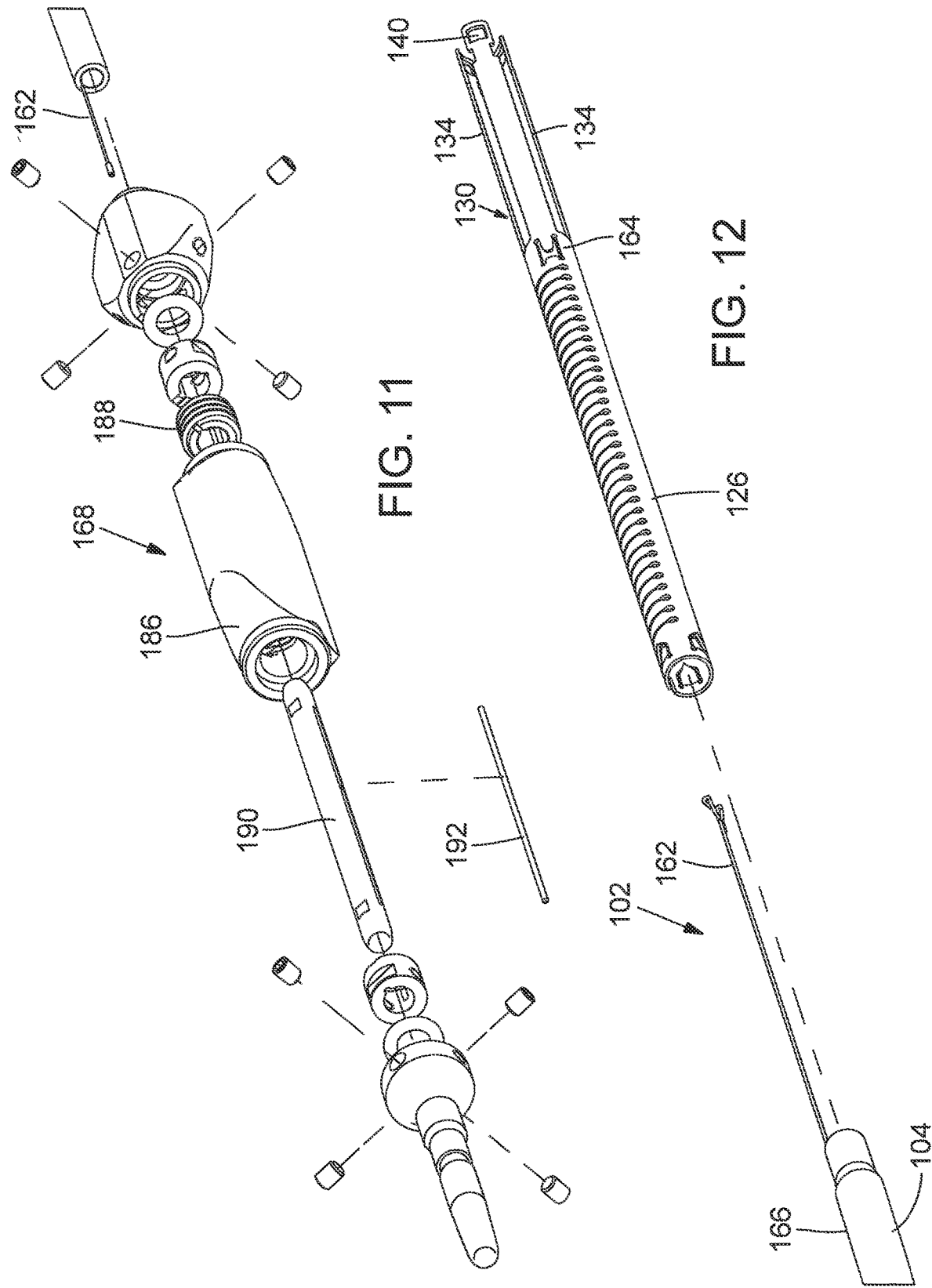

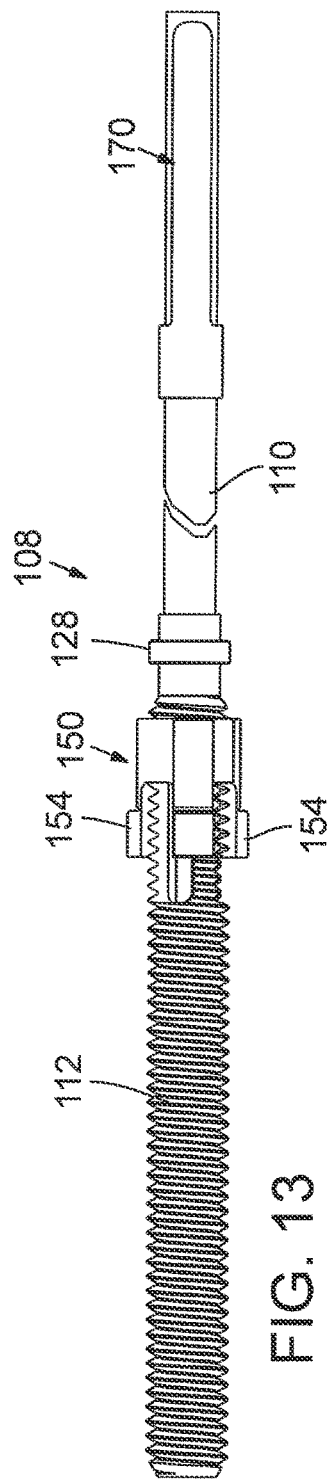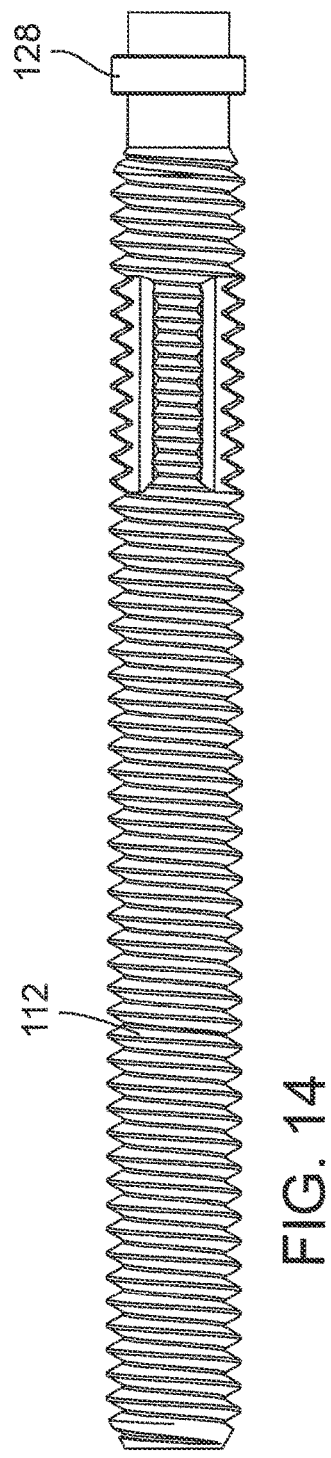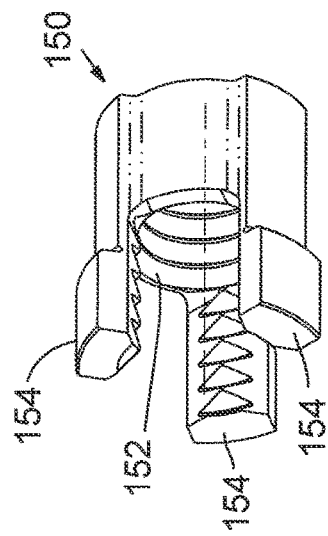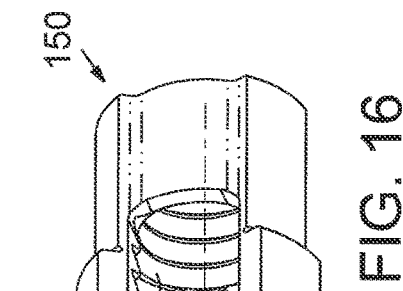

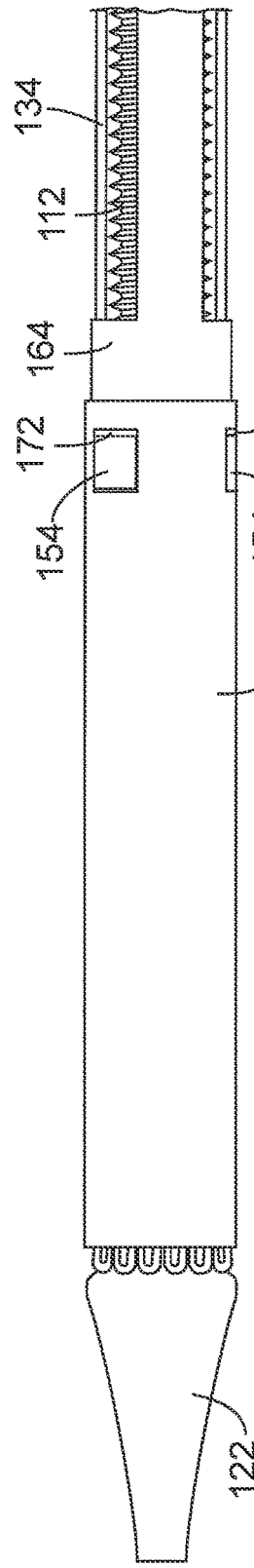
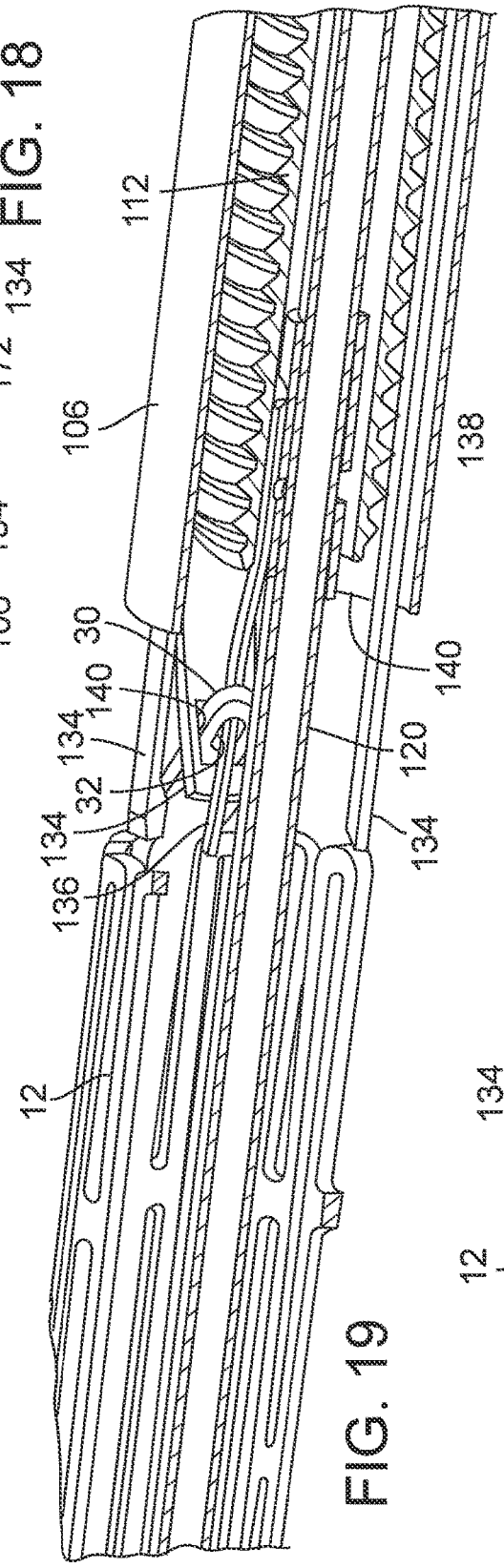
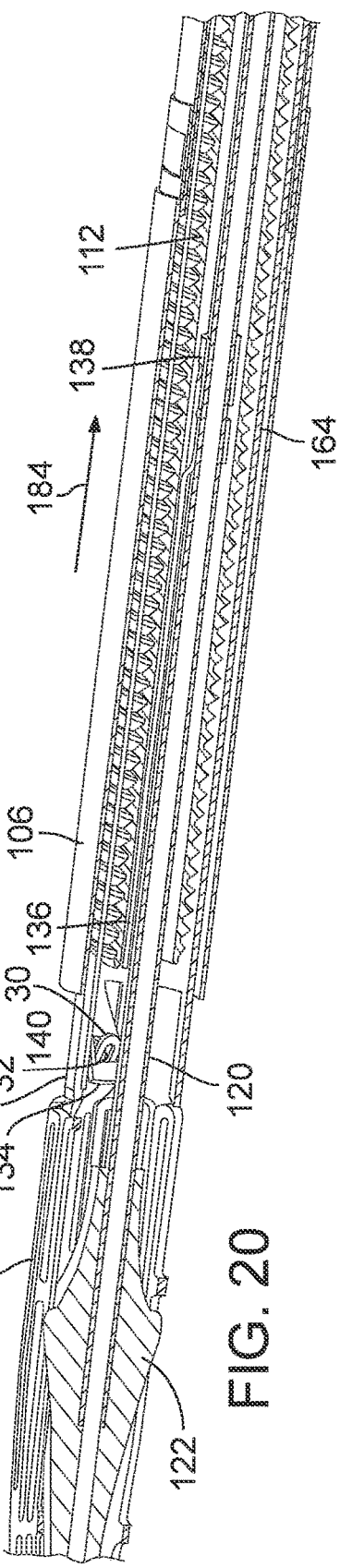
FIG. 18
FIG. 19
FIG. 20

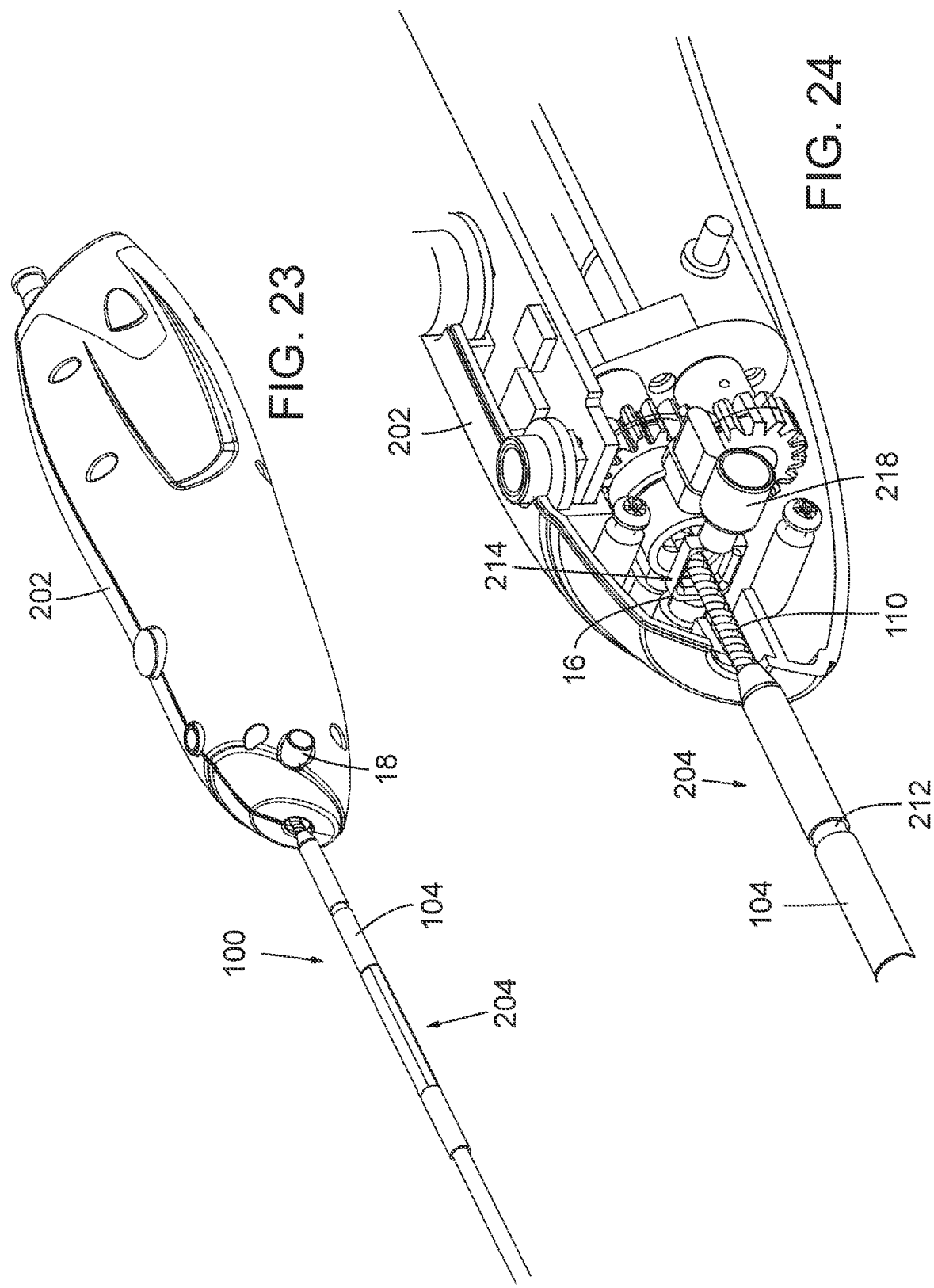

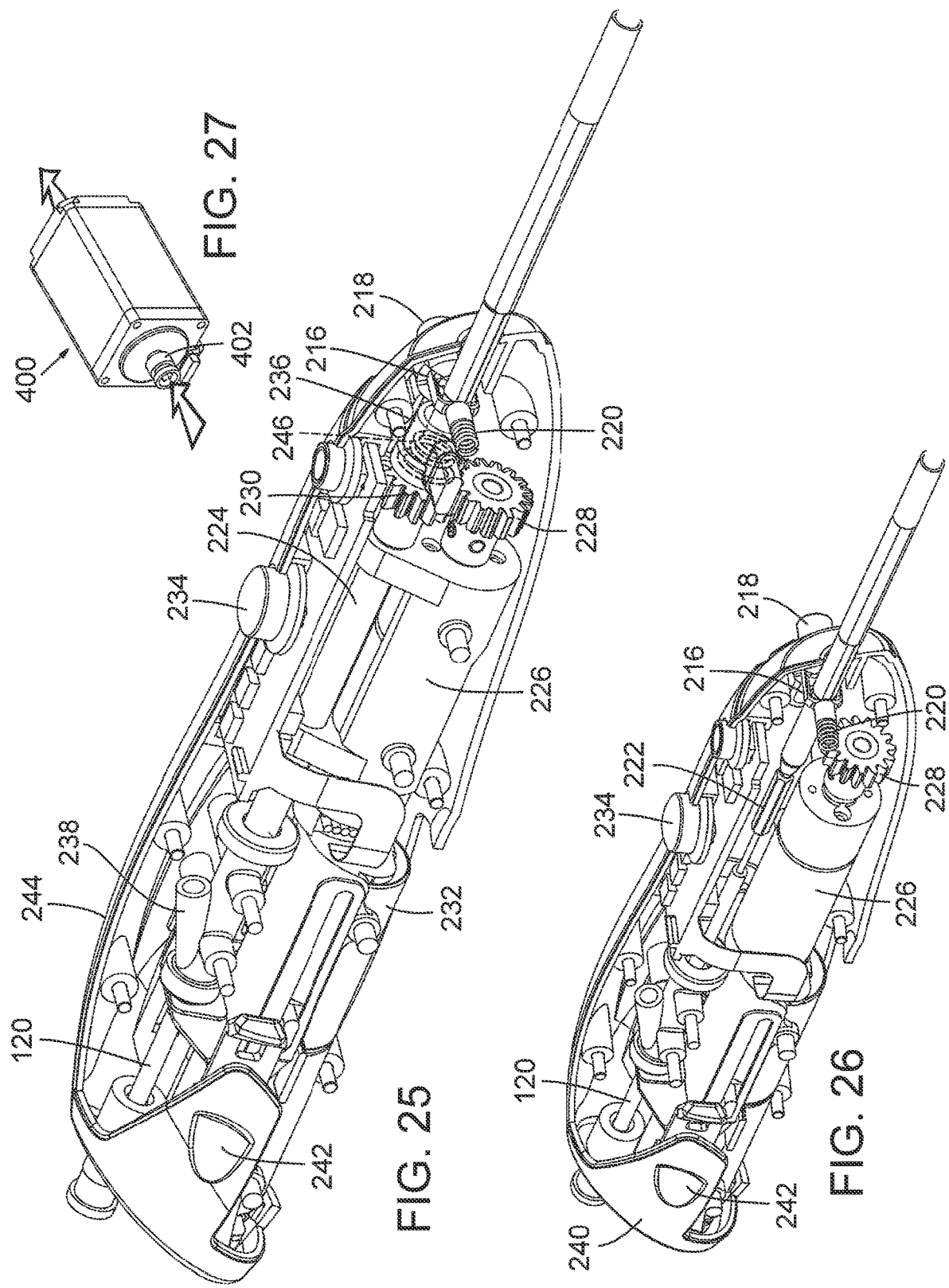

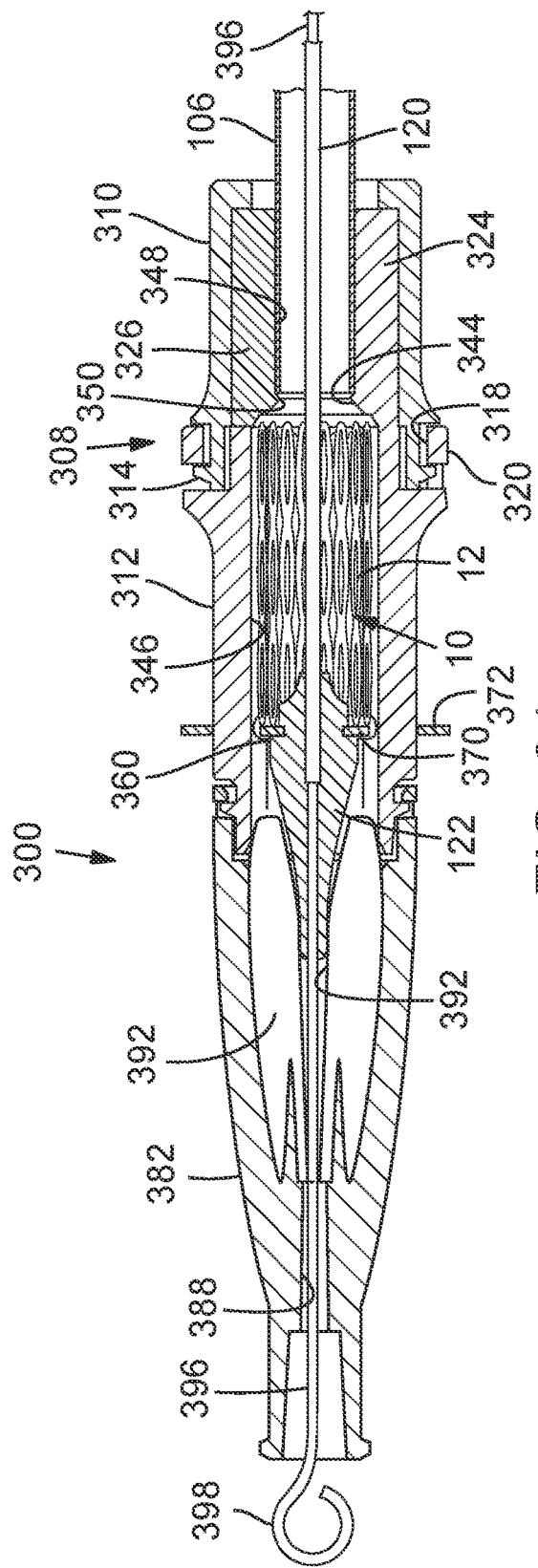
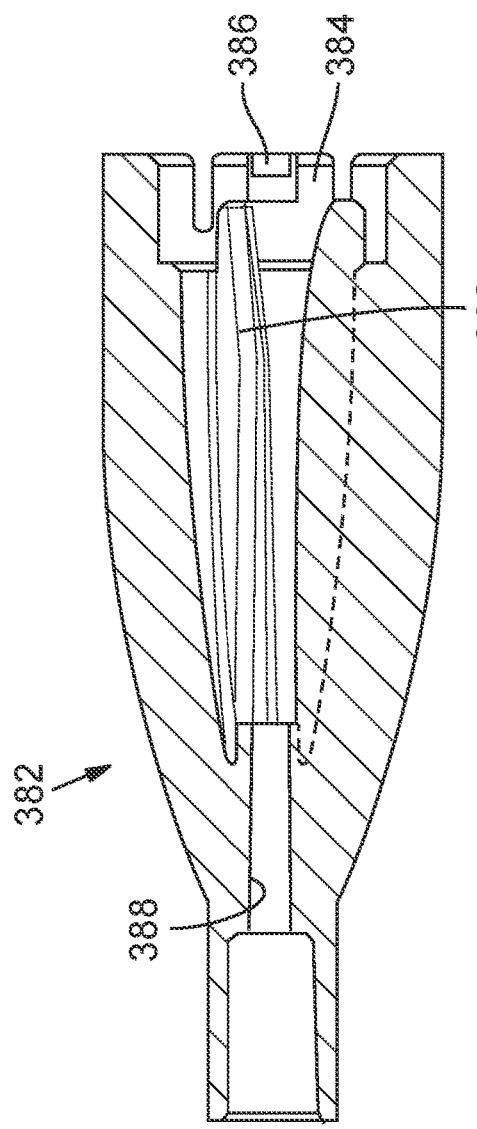
FIG. 31
FIG. 32

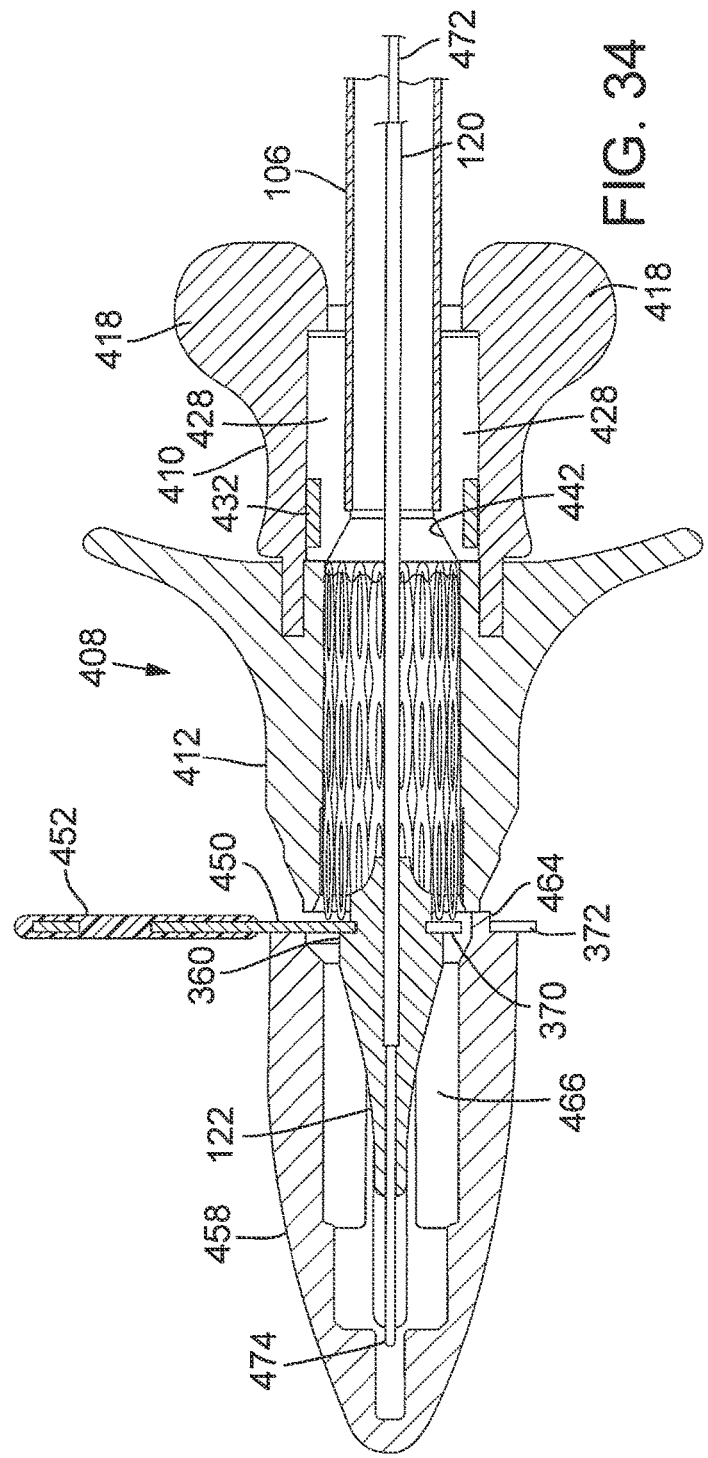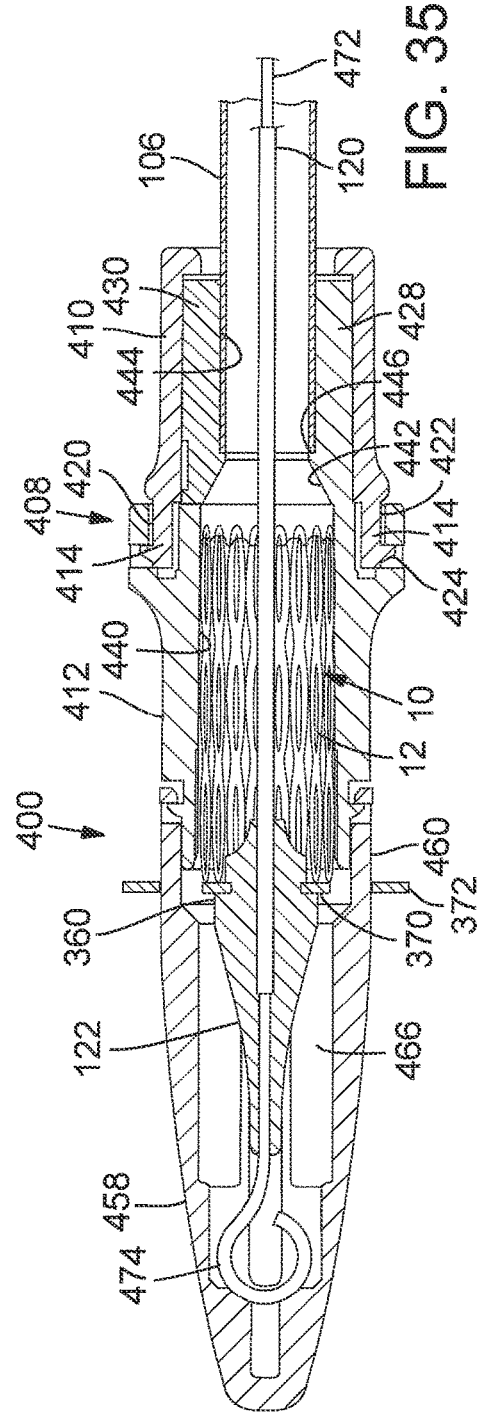

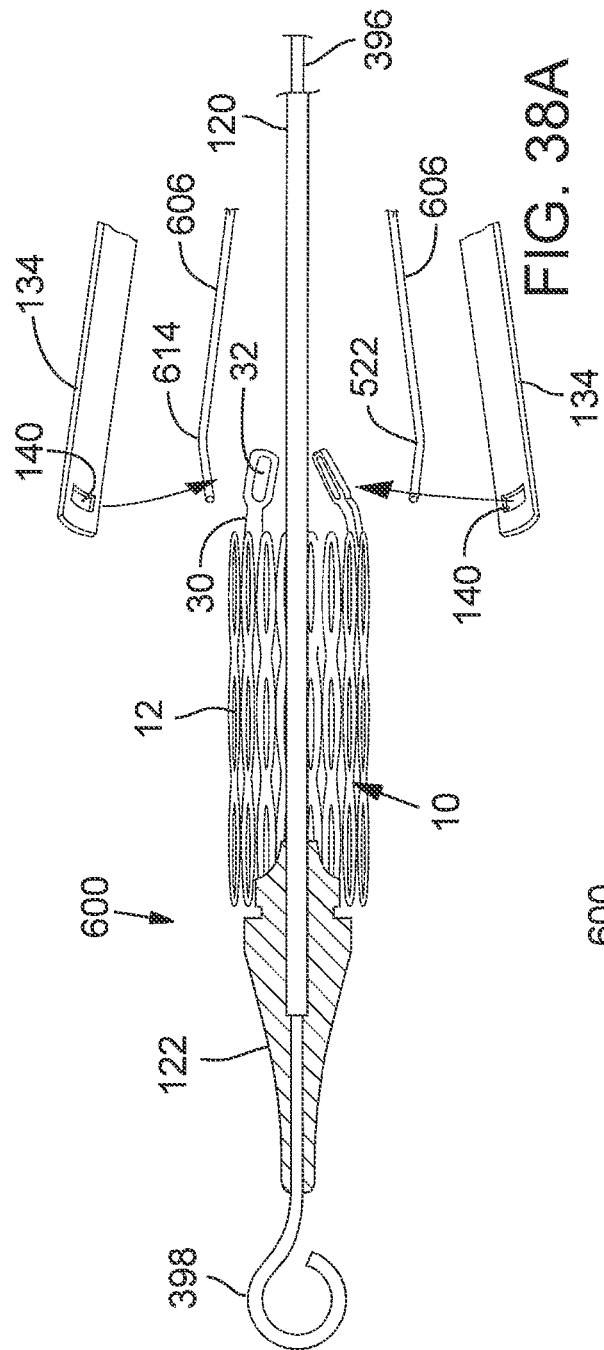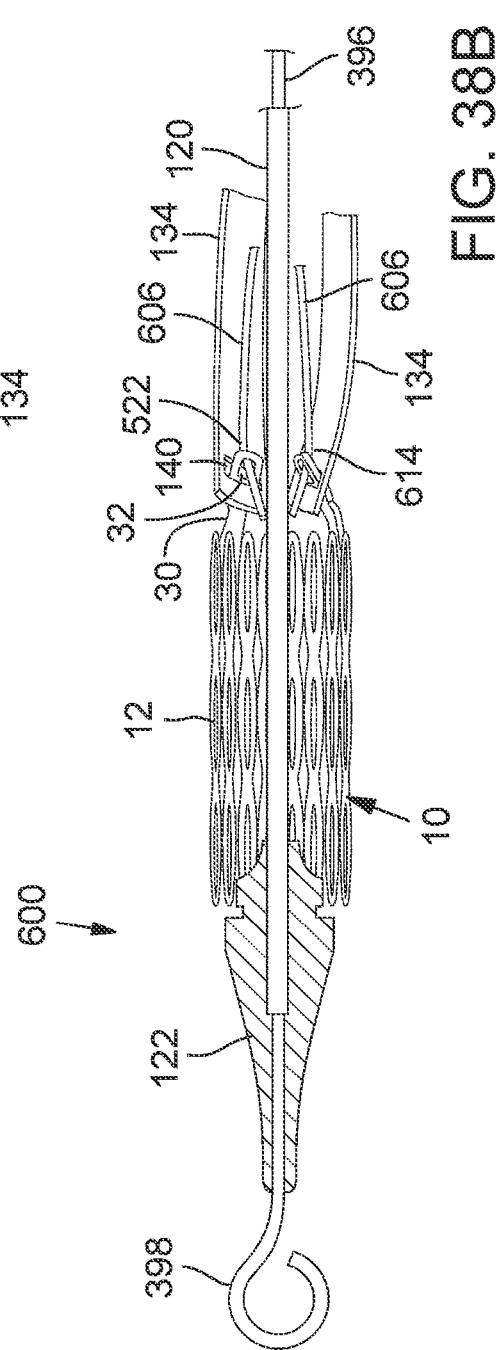

STORAGE ASSEMBLY FOR PROSTHETIC VALVE

CROSS REFERENCE TO RELATED APPLICATIONS

This application is a continuation of, and incorporates by reference, U.S. patent application Ser. No. 16/447,530, filed Jun. 20, 2019, now U.S. Pat. No. 11,273,024, which in turn is continuation of, and incorporates by reference, U.S. patent application Ser. No. 15/364,670, filed Nov. 30, 2016, now U.S. Pat. No. 10,357,351, which in turn claims the benefit of, and incorporates by reference, U.S. Provisional Patent Application No. 62/263,540, filed Dec. 4, 2015.

FIELD

The present disclosure relates to methods for maintaining the position of a nose cone relative to the frame of a prosthetic valve (e.g., prosthetic heart valve) in a delivery apparatus for implanting the prosthetic valve, and apparatus for carrying out such methods.

BACKGROUND

Prosthetic cardiac valves have been used for many years to treat cardiac valvular disorders. The native heart valves (such as the aortic, pulmonary, and mitral valves) serve critical functions in assuring the forward flow of an adequate supply of blood through the cardiovascular system. These heart valves can be rendered less effective by congenital, inflammatory, or infectious conditions. Such damage to the valves can result in serious cardiovascular compromise or death. For many years the definitive treatment for such disorders was the surgical repair or replacement of the valve during open heart surgery, but such surgeries are prone to many complications. More recently a transvascular technique has been developed for introducing and implanting a prosthetic heart valve using a flexible catheter in a manner that is less invasive than open heart surgery.

In this technique, a prosthetic valve is mounted in a crimped state on the end portion of a flexible catheter and advanced through a blood vessel of the patient until the prosthetic valve reaches the implantation site. The prosthetic valve at the catheter tip is then expanded to its functional size at the site of the defective native valve, such as by inflating a balloon on which the prosthetic valve is mounted. Alternatively, the prosthetic valve can have a resilient, self-expanding stent or frame that expands the prosthetic valve to its functional size when it is advanced from a delivery sheath at the distal end of the catheter.

A nose cone is typically located at the distal end of the catheter, providing for atraumatic tracking of the catheter and its associated components through the patient's vasculature. The nose cone is desirably positioned proximate the frame supporting the valve. If the nose cone is not positioned properly with respect to the frame, gaps or exposed frame edges may cause injury to the patient, or otherwise interfere with valve delivery. The position of the nose cone can typically vary from its initial position, such as during manufacturing, shipping, storage, or preparation of a device that includes the nose cone and frame.

SUMMARY

Certain embodiments of the present disclosure provide a prosthetic valve delivery assembly that includes a storage tube. The assembly includes a prosthetic heart valve that includes a frame having a distal portion and a proximal portion. The valve is at least partially disposed within the storage tube, such as being disposed in the storage tube or at least substantially disposed within the storage tube. The assembly further includes a nose cone having a proximal end and a distal end and disposed about an elongated shaft that extends through the storage tube. A removable tab is disposed between the distal frame portion and the nose cone. The tab assists in maintaining the position of the nose cone relative to the distal end of the frame.

In a particular implementation, the tab includes a proximal portion configured to be grasped by a user and a distal portion configured to be inserted about the proximal end of the nose cone. The distal portion defines a pair of arms. The arms engage the proximal end of the nose cone. For example, the nose cone may include a distal, conical, portion extending from a distal apex to a base and an intermediate portion extending proximally from the base. The diameter of the intermediate portion proximate the base is smaller than a diameter of the base of the distal portion of the nose cone. The arms are disposed about the intermediate portion of the nose cone.

In another implementation, the storage tube has an outer surface that defines a radial slot configured to receive the arms of the tab. In a particular example, the storage tube includes a pair of slots in opposing sides of the storage tube, such that the arms can be inserted through a first slot and out of a second slot. According to another example, the valve is positioned proximally relative to the slot, such that the tab arms restrain the valve against distal movement when the tab arms are inserted through the slot.

According to another aspect, the distal end of the frame extends beyond the distal end of the storage tube. The nose cone is positioned such that a proximal face of the tab abuts the frame when the arms are inserted about the proximal end of the nose cone.

According to another embodiment, the present disclosure provides a tab, including a tab that may be used with the prosthetic valve delivery assembly described above. The tab includes a pair of outer arms extending about a pair of inner arms. The outer arms engage an outer surface of the assembly. In a particular example, the outer arms extend radially about, and engage, an outer surface of the storage tube. In another example, the assembly includes a nose cone cap that engages the distal end of the nose cone. The outer arms extend radially about, and engage, the outer surface of the nose cone cap.

According to another embodiment of a tab, including a tab that may be used with the prosthetic valve delivery assembly described above, the tab includes a pair of arms located at a distal end of the tab and configured to be inserted about a nose cone. A proximal portion of the tab defines a gripping surface that is configured to assist a user in gripping the tab. In one example, the gripping surface is thicker than the distal portion of the tab. The tab may include additional features to assist gripability, such as one or more embossed ridges. According to another example, the gripping surface is configured to indicate to a user that the tab should be removed, such as having a triangular shape with a distal apex. The gripping surface may also be formed with other visual indications to draw attention to the tab, such as forming it from, or coating it with, a brightly colored material.

The present disclosure also provides a nose cone cap, which may be used in the above-described prosthetic valve delivery assembly. The nose cone cap extends over at least a distal portion of the nose cone and is releasably coupled to a distal end of a storage tube. In some implementations, the nose cone cap is generally conical and includes a distal apex and a proximal base. In particular implementations, the base includes at least one proximally extending arm comprising a locking mechanism to engage a mating locking mechanism on the storage tube of the prosthetic valve delivery assembly. For example, the nose cone cap and storage tube may include mating slots and tabs.

In further implementations, the nose cone cap is configured to receive the tab, such as arms of the tab. In a particular example, the nose cone cap can include a tab arm extending proximally from the base of the nose cone cap. The tab arm is dimensioned such that the tab arms extend about the lateral sides of the nose cone cap tab arm. In a more particular example, the nose cone cap, at the side opposite the tab arm, includes an aperture for receiving the tab. For example, the base may define a recess at the proximal end of the base.

In yet another implementation, the interior of the nose cone cap includes a plurality of axially and radially extending fins defining a cavity for receiving at least a distal end portion of a nose cone. In at least certain examples, the fins are tapered, such that a cavity formed by the fins is larger at the base of those cone cap than at a distal portion of the nose cone cap.

The fins may be configured, for example, to define a cavity dimensioned to receive a proximal portion of the nose cone. When the nose cone cap is coupled to the storage tube, the fins help limit distal movement of the nose cone relative to the storage tube.

In particular implementations, the nose cone cap is configured to be used with a valve delivery assembly that includes a stylet. In one example, such as a nose cone cap that includes internal fins, the nose cone cap defines an internal recess configured to receive a distal end of the stylet. For example, the recess may receive a loop located at the distal end of the stylet. The stylet is positioned between the fins as it extends proximally through the nose cone cap.

In another example, the nose cone cap includes an axial bore for receiving the stylet. The bore may be dimensioned such that it has a smaller diameter than a distal loop of the stylet. Thus, the stylet is prevented from moving axially past the apex of the nose cone cap. In a particular example, the stylet is configured to be insertable proximally through the apex of the nose cone cap until the loop of the stylet abuts the apex of the nose cone cap.

In a further example, the nose cone cap includes a latch releasably coupled to a tether. The tether is coupled to the nose cone cap, such as extending through one or more apertures formed in the nose cone cap. A component of the latch or tether, such as a pin, is configured to be inserted through a loop located at the distal end of the stylet and coupled to the tether. When coupled to the tether, the latch and tether resist axial movement of the stylet.

In further embodiments, the present disclosure provides a method for securing the position of a nose cone relative to a prosthetic valve. A prosthetic valve is placed at least partially within a storage tube. A nose cone is positioned relative to the valve. A tab is inserted between at least a portion of the nose cone and the valve such that the nose cone is restrained from proximal movement relative to the tab. The tab, in one implementation, is inserted through a radially extending slot formed in an outer surface of the storage tube. In another implementation, the valve extends distally from the distal end of the storage tube and the tab is inserted such that it abuts the distal end of the valve.

In a particular implementation, the method includes placing a nose cone cap over a distal end portion of the nose cone and securing the nose cone cap to the storage tube. The nose cone is thus restrained by the nose cone cap from distal and/or proximal axial movement relative to the storage tube. In a particular example, the nose cone cap comprises internal fins and the nose cone is received in a cavity formed by the fins. The fins compress a distal portion of the nose cone proximally against the tab. In a further example, a stylet is inserted through the nose cone and the nose cone cap is inserted over the stylet. In one aspect, the stylet includes a loop at its distal end, and the loop is received by a recess formed in the nose cone cap. In another example, the stylet is inserted proximally through a distal apex of the nose cone cap into an axial bore, wherein the axial bore has a diameter smaller than the diameter of a loop located at the distal end of the stylet. In a further example, a tether is inserted through the loop of the stylet and releasably coupled to a latch, wherein the tether is further secured to the nose cone. The latch and tether provide resistance against axial movement of the stylet.

The method, in further implementations, includes inserting tab arms about an exterior surface of a prosthetic valve delivery assembly. In one example, the arms are inserted about an exterior surface of the storage tube. In another example, the arms are inserted about an exterior surface of a nose cone cap coupled to the storage tube.

In another embodiment, the present disclosure provides a prosthetic valve delivery assembly that includes a stylet, a nose cone coupled to an elongated shaft, and a prosthetic heart valve disposed about the elongated shaft. The stylet inserted through a lumen of the nose cone and a lumen of the elongated shaft. The stylet includes at least one bend that is located in, and engages, at least one of the nose cone lumen and the elongated shaft lumen. In various examples, the stylet bend is located in the nose cone lumen, the elongated shaft lumen, or both the elongated shaft and nose cone lumens. In at least one implementation, the stylet includes a plurality of bends.

In another embodiment, the present disclosure provides a valve-retention assembly useable with a prosthetic heart valve delivery assembly. The valve-retention assembly includes a release member that includes at least one release prong defining an aperture proximate a distal end of the release prong, a locking member that includes at least one locking arm, and a prosthetic heart valve that includes a frame having at least one aperture formed in a proximal retaining arm of the frame and configured to be inserted through the aperture of the release prong. The locking member is coupled to an elongated shaft that includes a nose cone. The locking arm defines a bend at a distal portion of the locking arm. The valve retaining arm is inserted through the aperture of the release prong. The locking arm is inserted through the aperture of the valve retaining arm, such that a portion of the valve retaining arm proximate the aperture of the valve retaining arm is received in the bend of the locking arm, thus providing resistance to longitudinal movement of the valve.

There are additional features and advantages of the various embodiments of the present disclosure. They will become evident from the following disclosure.

In this regard, it is to be understood that this is a summary of the various embodiments described herein. Any given embodiment of the present disclosure need not provide all features noted above, nor must it solve all problems or address all issues in the prior art noted above.

BRIEF DESCRIPTION OF THE DRAWINGS

Various embodiments are shown and described in connection with the following drawings in which:

FIG. 8 is a cross-sectional view of an embodiment of a delivery apparatus that can be used to deliver and implant a prosthetic valve, such as the prosthetic valve shown in FIG. 1.

FIG. 9 is an exploded view of the delivery apparatus of FIG. 8.

FIG. 10 is a side view of the guide catheter of the delivery apparatus of FIG. 8.

FIG. 11 is a perspective, exploded view of the proximal end portion of the guide catheter of FIG. 10.

FIG. 12 is a perspective, exploded view of the distal end portion of the guide catheter of FIG. 10.

FIG. 13 is a side view of the torque shaft catheter of the delivery apparatus of FIG. 8.

FIG. 14 is an enlarged side view of the rotatable screw of the torque shaft catheter of FIG. 13.

FIG. 15 is an enlarged perspective view of a coupling member disposed at the end of the torque shaft.

FIG. 16 is an enlarged perspective view of the threaded nut used in the torque shaft catheter of FIG. 13.

FIG. 18 is an enlarged side view of the distal end portion of the delivery apparatus of FIG. 8 showing the delivery sheath in a delivery position covering a prosthetic valve in a compressed state for delivery into a patient.

FIG. 19 is an enlarged cross-sectional view of a section of the distal end portion of the delivery apparatus of FIG. 8 showing the valve-retaining mechanism securing the stent of a prosthetic valve to the delivery apparatus.

FIG. 20 is an enlarged cross-sectional view similar to FIG. 19, showing the inner fork of the valve-retaining mechanism in a release position for releasing the prosthetic valve from the delivery apparatus.

FIGS. 23-26 are various views of an embodiment of a motorized delivery apparatus that can be used to operate the torque shaft of the delivery apparatus shown in FIG. 8.

FIG. 27 is a perspective view of an alternative motor that can be used to operate the torque shaft of the delivery apparatus shown in FIG. 8.

FIG. 31 is an enlarged cross-sectional view of the valve storage assembly of FIG. 30.

FIG. 32 is an enlarged cross-sectional view of a nose cone cap useable with the valve storage assembly of FIGS. 30 and 31.

FIG. 34 is an enlarged cross-sectional view of the valve storage assembly of FIG. 32, taken through the longitudinal axis of the tab.

FIG. 35 is an enlarged cross-sectional view of the valve storage assembly of FIG. 32, taken through a transverse axis of the tab.

FIG. 38A is a side view of a valve-retaining mechanism useable with the delivery apparatus of FIG. 8, showing the components in a disengaged state.

FIG. 38B is a side view of the valve-retaining mechanism of FIG. 38A, showing the components in a locked configuration.

DETAILED DESCRIPTION

Figure 1:
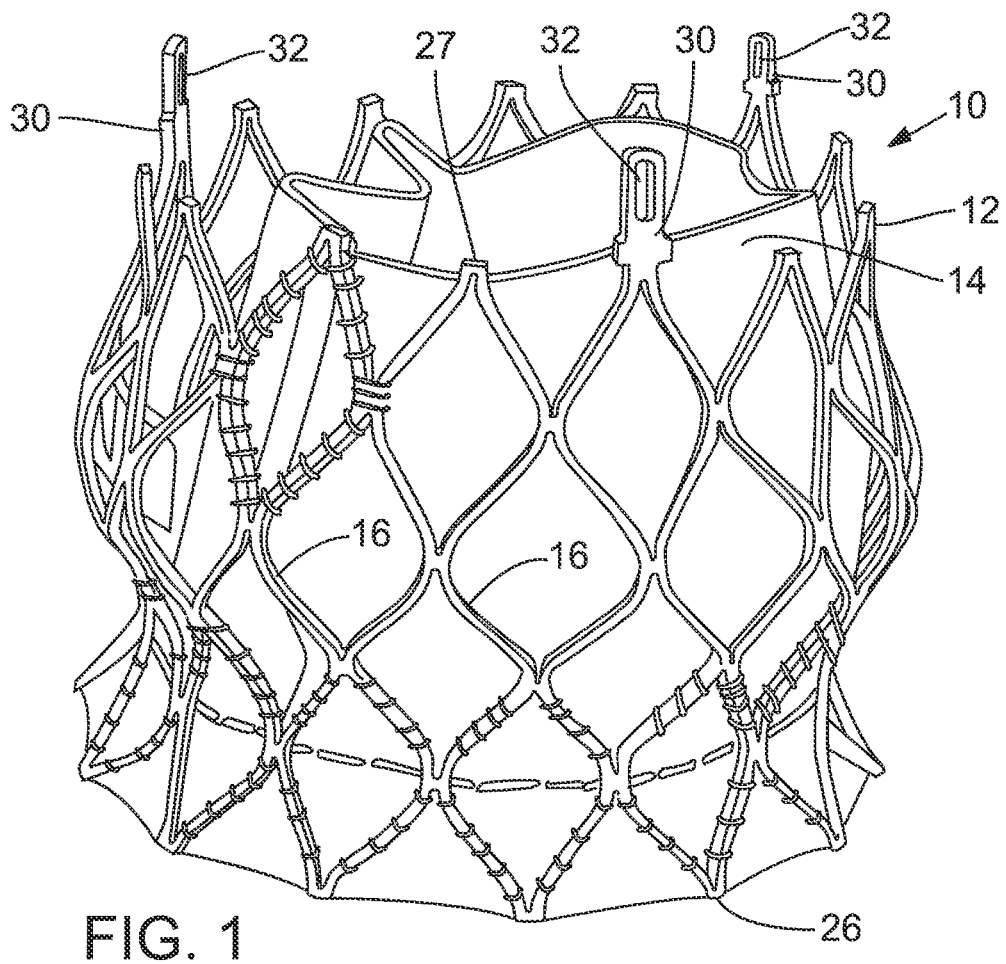
FIG. 1 is a perspective view of a prosthetic valve that can be used to replace the native aortic valve of the heart, according to one embodiment.

Referring first to FIG. 1, there is shown a prosthetic aortic heart valve 10, according to one embodiment. The prosthetic valve 10 includes an expandable frame member, or stent, 12 that supports a flexible leaflet section 14. The prosthetic valve 10 is radially compressible to a compressed state for delivery through the body to a deployment site and expandable to its functional size shown in FIG. 1 at the deployment site. In certain embodiments, the prosthetic valve 10 is self-expanding; that is, the prosthetic valve can radially expand to its functional size when advanced from the distal end of a delivery sheath. Apparatuses particularly suited for percutaneous delivery and implantation of a self-expanding prosthetic valve are described in detail below. In other embodiments, the prosthetic valve can be a balloon-expandable prosthetic valve that can be adapted to be mounted in a compressed state on the balloon of a delivery catheter. The prosthetic valve can be expanded to its functional size at a deployment site by inflating the balloon, as known in the art.

The illustrated prosthetic valve 10 is adapted to be deployed in the native aortic annulus, although it also can be used to replace the other native valves of the heart. Moreover, the prosthetic valve 10 can be adapted to replace other valves within the body, such venous valves.

Figure 3:
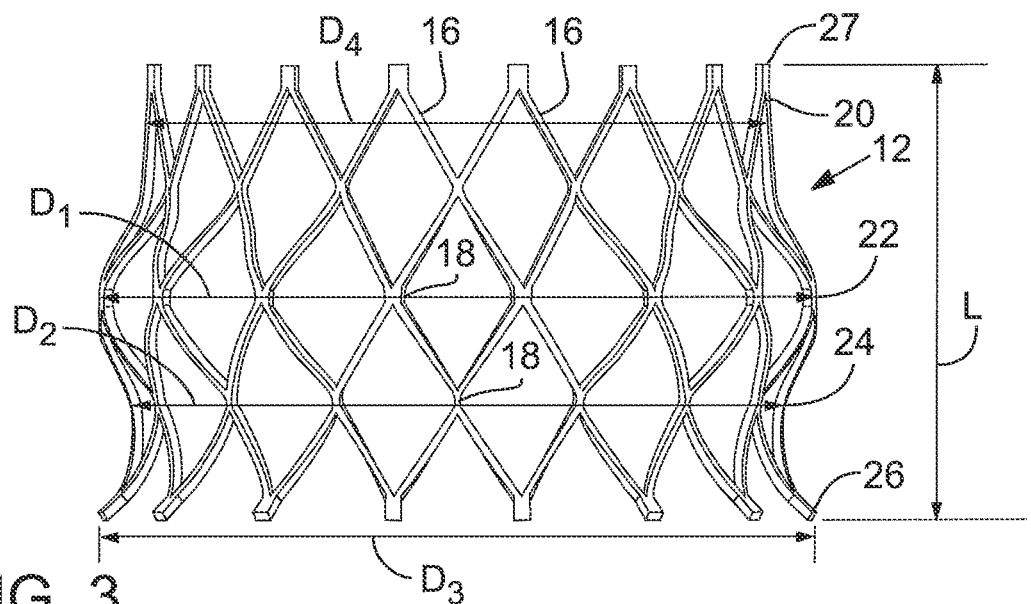
FIG. 3 is side elevation view of the support frame of the prosthetic valve of FIG. 1.
Figure 4:
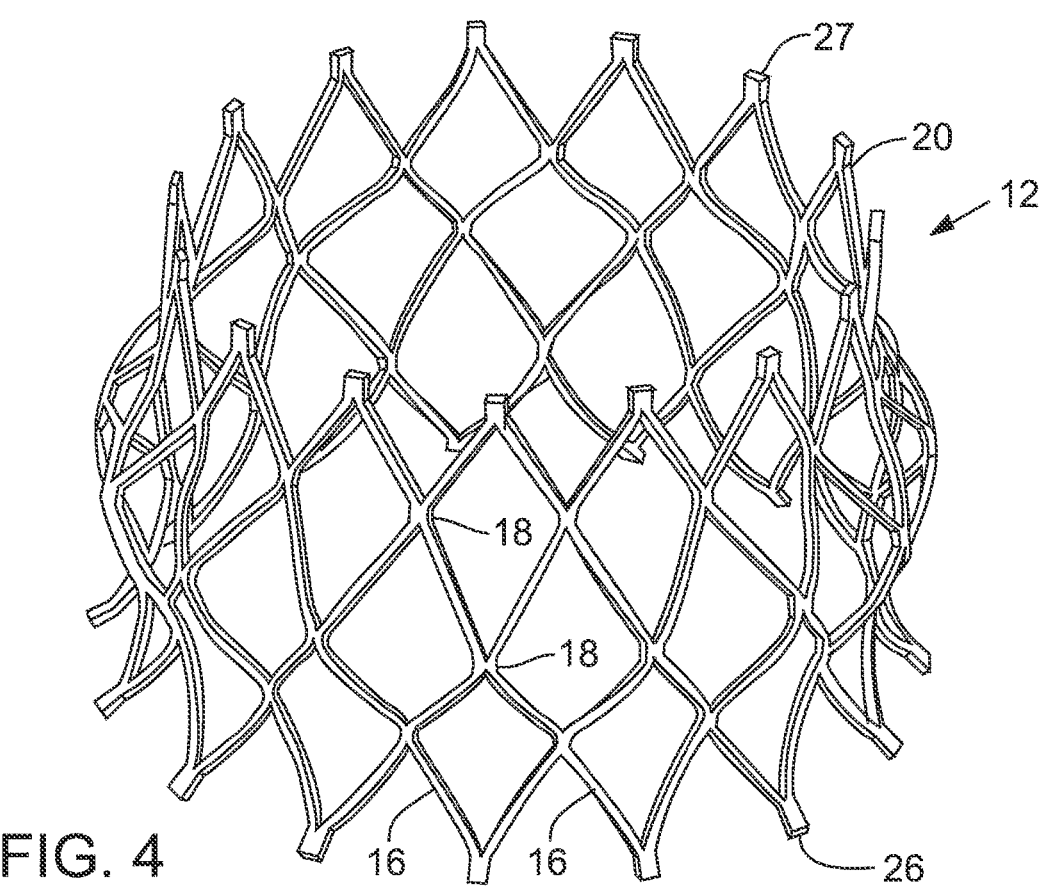
FIG. 4 is a perspective view of the support frame of the prosthetic valve of FIG. 1.

FIGS. 3 and 4 show the stent 12 without the leaflet section 14 for purposes of illustration. As shown, the stent 12 can be formed from a plurality of longitudinally extending, generally sinusoidal shaped frame members, or struts, 16. The struts 16 are formed with alternating bends and are welded or otherwise secured to each other at nodes 18 formed from the vertices of adjacent bends so as to form a mesh structure. The struts 16 can be made of a suitable shape memory material, such as the nickel titanium alloy known as Nitinol, that allows the prosthetic valve to be compressed to a reduced diameter for delivery in a delivery apparatus (such as described below) and then causes the prosthetic valve to expand to its functional size inside the patient's body when deployed from the delivery apparatus. If the prosthetic valve is a balloon-expandable prosthetic valve that is adapted to be crimped onto an inflatable balloon of a delivery apparatus and expanded to its functional size by inflation of the balloon, the stent 12 can be made of a suitable ductile material, such as stainless steel.

The stent 12 has an inflow end 26 and an outflow end 27. The mesh structure formed by struts 16 comprises a generally cylindrical "upper" or outflow end portion 20, an outwardly bowed or distended intermediate section 22, and an inwardly bowed "lower" or inflow end portion 24. The intermediate section 22 desirably is sized and shaped to extend into the Valsalva sinuses in the root of the aorta to assist in anchoring the prosthetic valve in place once implanted. As shown, the mesh structure desirably has a curved shape along its entire length that gradually increases in diameter from the outflow end portion 20 to the intermediate section 22, then gradually decreases in diameter from the intermediate section 22 to a location on the inflow end portion 24, and then gradually increases in diameter to form a flared portion terminating at the inflow end 26.

When the prosthetic valve 10 is in its expanded state, the intermediate section 22 has a diameter $D_1$, the inflow end portion 24 has a minimum diameter $D_2$, the inflow end 26 has a diameter $D_3$, and the outflow end portion 20 has a diameter $D_4$, where $D_2$ is less than $D_1$ and $D_3$, and $D_4$ is less than $D_2$. In addition, $D_1$ and $D_3$ desirably are greater than the diameter of the native annulus in which the prosthetic valve is to be implanted. In this manner, the overall shape of the stent 12 assists in retaining the prosthetic valve at the implantation site.

Figure 5A:
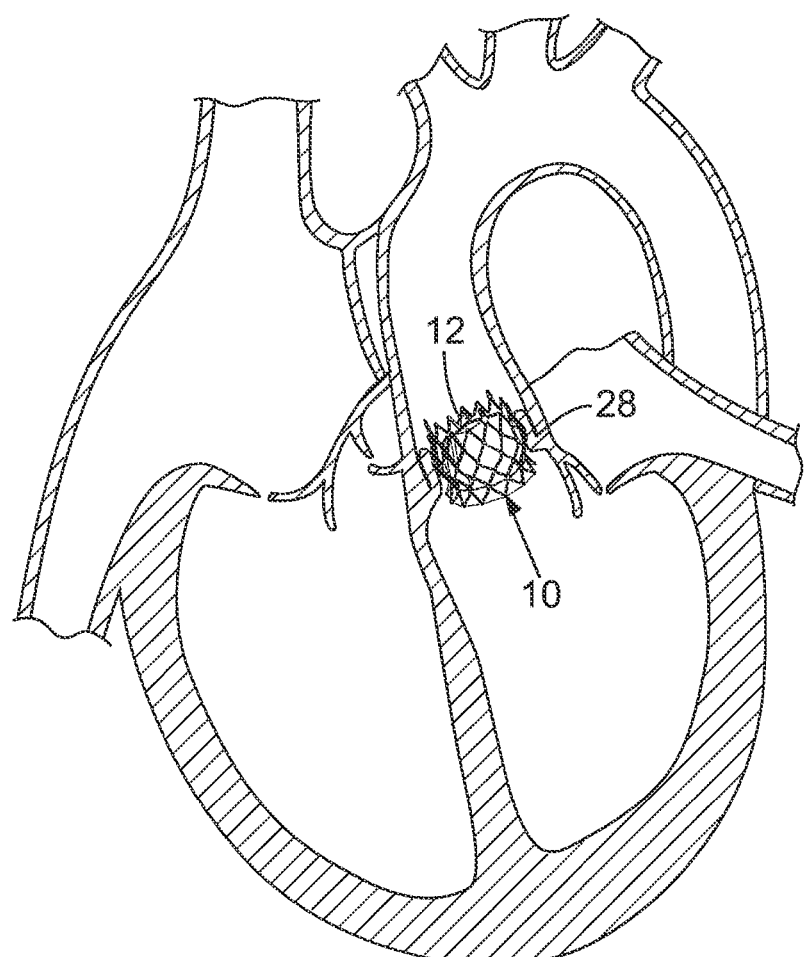
FIG. 5A is a cross-sectional view of the heart showing the prosthetic valve of FIG. 1 implanted within the aortic annulus.
Figure 5B:
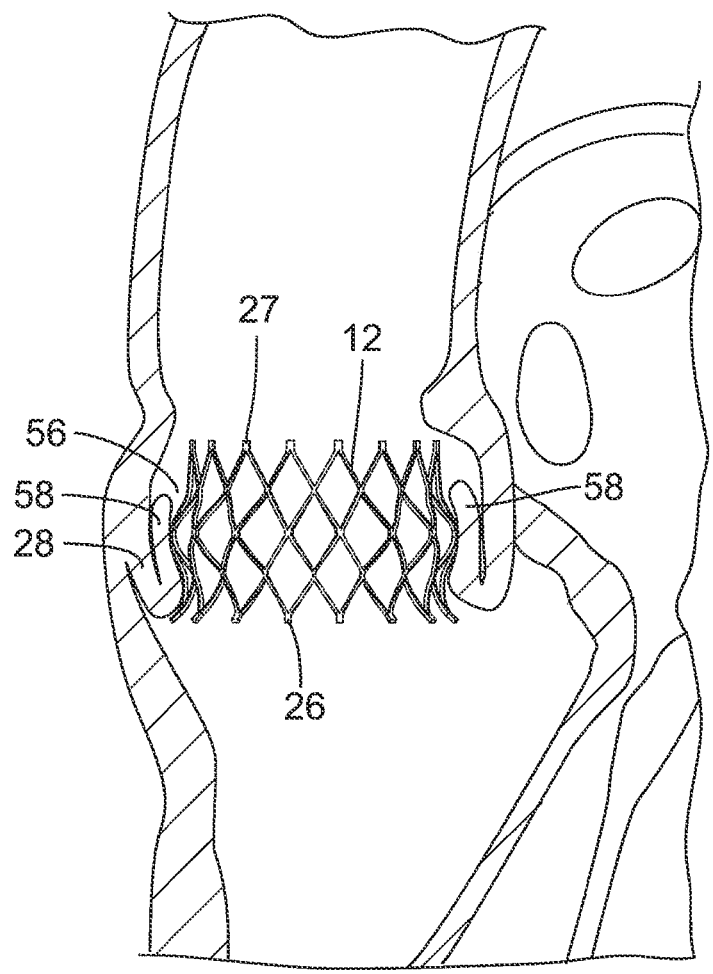
FIG. 5B is an enlarged view of FIG. 5A illustrating the prosthetic valve implanted within the aortic annulus, shown with the leaflet structure of the prosthetic valve removed for clarity.

More specifically, and referring to FIGS. 5A and 5B, the prosthetic valve 10 can be implanted within a native valve (the aortic valve in the illustrated example) such that the lower section 24 is positioned within the aortic annulus 28, the intermediate section 22 extends above the aortic annulus into the Valsalva's sinuses 56, and the lower flared end 26 extends below the aortic annulus. The prosthetic valve 10 is retained within the native valve by the radial outward force of the lower section 26 against the surrounding tissue of the aortic annulus 28 as well as the geometry of the stent 12. Specifically, the intermediate section 22 and the flared lower end 26 extend radially outwardly beyond the aortic annulus 28 to better resist against axial dislodgement of the prosthetic valve 10 in the upstream and downstream directions (toward and away from the aorta). Depending on the condition of the native leaflets 58, the prosthetic valve 10 typically is deployed within the native annulus 28 with the native leaflets 58 folded upwardly and compressed between the outer surface of the stent 12 and the walls of the Valsalva sinuses 56, as depicted in FIG. 5B. In some cases, it may be desirable to excise the leaflets 58 prior to implanting the prosthetic valve 10.

Known prosthetic valves having a self-expanding frame typically have additional anchoring devices or frame portions that extend into and become fixed to non-diseased areas of the vasculature. Because the shape of the stent 12 assists in retaining the prosthetic valve, additional anchoring devices are not required and the overall length L of the stent can be minimized to prevent the stent upper portion 20 from extending into the non-diseased area of the aorta, or to at least minimize the extent to which the upper portion 20 extends into the non-diseased area of the aorta. Avoiding the non-diseased area of the patient's vasculature helps avoid complications if future intervention is required. For example, the prosthetic valve can be more easily removed from the patient because the stent is primarily anchored to the diseased part of the native valve. Furthermore, a shorter prosthetic valve is more easily navigated around the aortic arch.

In particular embodiments, for a prosthetic valve intended for use in a 22-mm to 24-mm annulus, the diameter $D_1$ is about 28 mm to about 32 mm, with 30 mm being a specific example; the diameter $D_2$ is about 24 mm to about 28 mm, with 26 mm being a specific example; the diameter $D_3$ is about 28 mm to about 32 mm, with 30 mm being a specific example; and the diameter $D_4$ is about 24 mm to about 28 mm, with 26 mm being a specific example. The length L in particular embodiments is about 20 mm to about 24 mm, with 22 mm being a specific example.

Referring again to FIG. 1, the stent 12 can have a plurality of angularly spaced retaining arms, or projections, in the form of posts 30 (three in the illustrated embodiment) that extend from the stent upper portion 20. Each retaining arm 30 has a respective aperture 32 that is sized to receive prongs of a valve-retaining mechanism that can be used to form a releasable connection between the prosthetic valve and a delivery apparatus (described below). In alternative embodiments, the retaining arms 30 need not be provided if a valve-retaining mechanism is not used.

Figure 6:
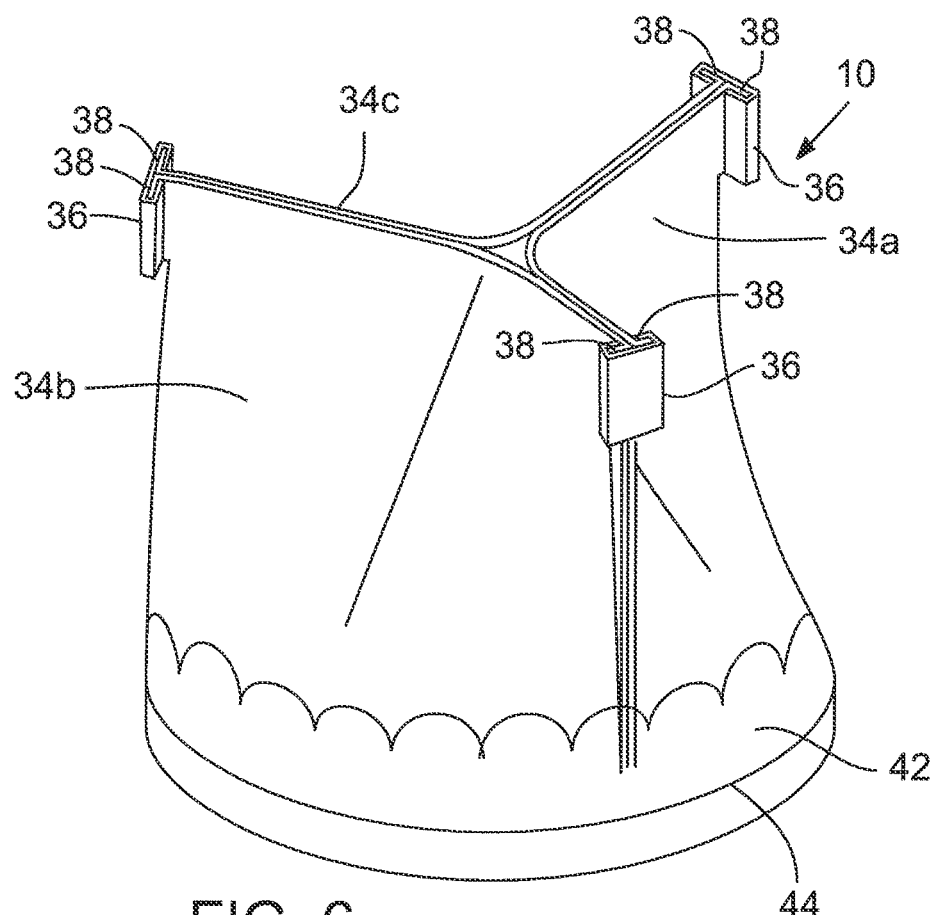
FIG. 6 is a perspective view of the leaflet structure of the prosthetic valve of FIG. 1 shown prior to being secured to the support frame.
Figure 7:
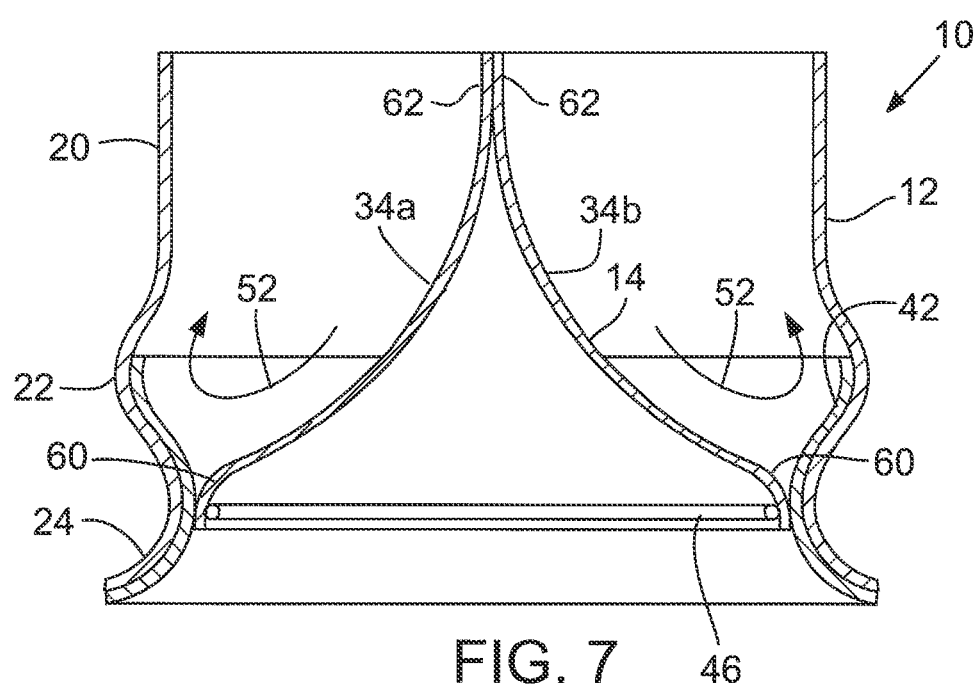
FIG. 7 is a cross-sectional view of the prosthetic valve of FIG. 1.

As best shown in FIGS. 6 and 7, the leaflet assembly 14 in the illustrated embodiment comprises three leaflets 34a, 34b, 34c made of a flexible material. Each leaflet has an inflow end portion 60 and an outflow end portion 62. The leaflets can comprise any suitable biological material (e.g., pericardial tissue, such as bovine or equine pericardium), bio-compatible synthetic materials, or other such materials, such as those described in U.S. Pat. No. 6,730,118, which is incorporated herein by reference. The leaflet assembly 14 can include an annular reinforcing skirt 42 that is secured to the outer surfaces of the inflow end portions of the leaflets 34a, 34b, 34c at a suture line 44 adjacent the inflow end of the prosthetic valve. The inflow end portion of the leaflet assembly 14 can be secured to the stent 12 by suturing the skirt 42 to struts 16 of the lower section 24 of the stent (best shown in FIG. 3). As shown in FIG. 7, the leaflet assembly 14 can further include an inner reinforcing strip 46 that is secured to the inner surfaces of the inflow end portions 60 of the leaflets.

Figure 2:
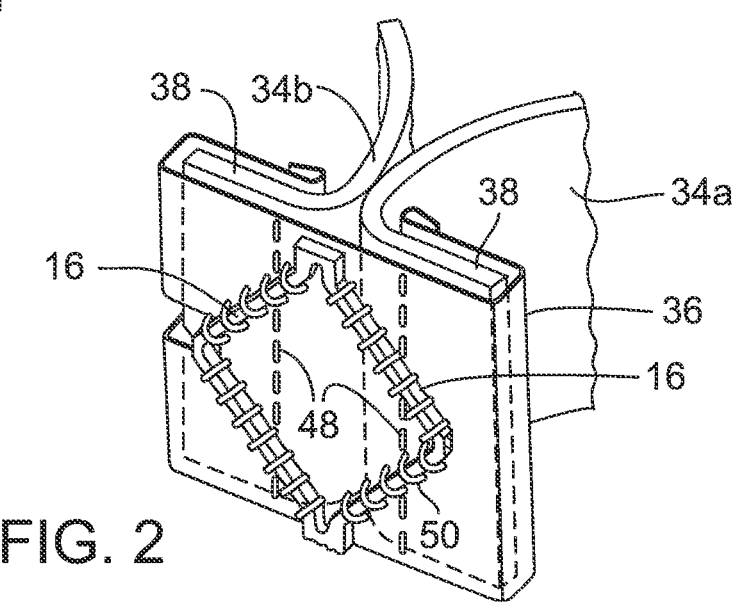
FIG. 2 is a perspective view of a portion of the prosthetic valve of FIG. 1 illustrating the connection of two leaflets to the support frame of the prosthetic valve.

Referring again to FIGS. 1 and 2, the outflow end portion of the leaflet assembly 14 can be secured to the upper portion of the stent 12 at three angularly spaced commissure attachments of the leaflets 34a, 34b, 34c. As best shown in FIG. 2, each commissure attachment can be formed by wrapping a reinforcing section 36 around adjacent upper edge portions 38 of a pair of leaflets at the commissure formed by the two leaflets and securing the reinforcing section 36 to the edge portions 38 with sutures 48. The sandwiched layers of the reinforcing material and leaflets can then be secured to the struts 16 of the stent 12 with sutures 50 adjacent the outflow end 27 of the stent. The leaflets therefore desirably extend the entire length or substantially the entire length of the stent 12 from the inflow end 26 to the outflow end 27. The reinforcing sections 36 reinforce the attachment of the leaflets to the stent 12 so as to minimize stress concentrations at the suture lines and avoid "needle holes" on the portions of the leaflets that flex during use. The reinforcing sections 36, the skirt 42, and the inner reinforcing strip 46 desirably are made of a bio-compatible synthetic material, such as polytetrafluoroethylene (PTFE), or a woven fabric material, such as woven polyester (e.g., polyethylene terephtalate (PET)).

FIG. 7 shows the operation of the prosthetic valve 10. During diastole, the leaflets 34a, 34b, 34c collapse to effectively close the prosthetic valve. As shown, the curved shape of the intermediate section 22 of the stent 12 defines a space between the intermediate section and the leaflets that mimics the Valsalva sinuses. Thus, when the leaflets close, backflow entering the "sinuses" creates a turbulent flow of blood along the upper surfaces of the leaflets, as indicated by arrows 52. This turbulence assists in washing the leaflets and the skirt 42 to minimize clot formation.

The prosthetic valve 10 can be implanted in a retrograde approach where the prosthetic valve, mounted in a crimped state at the distal end of a delivery apparatus, is introduced into the body via the femoral artery and advanced through the aortic arch to the heart, as further described in U.S. Patent Publication No. 2008/0065011, which is incorporated herein by reference.

Figure 8A:
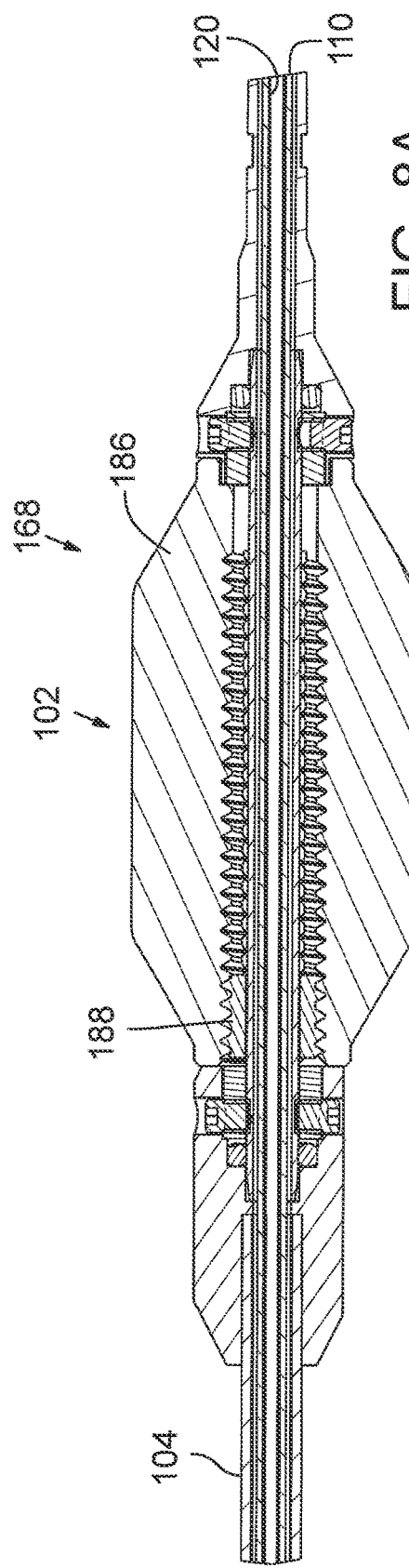
FIGS. 8A-8C are enlarged cross-sectional views of sections of FIG. 8.
Figure 8B:
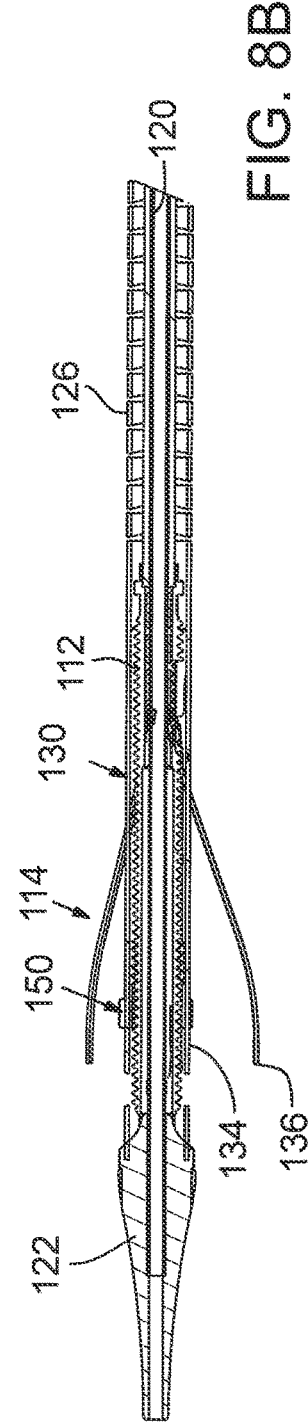
Figure 8C:
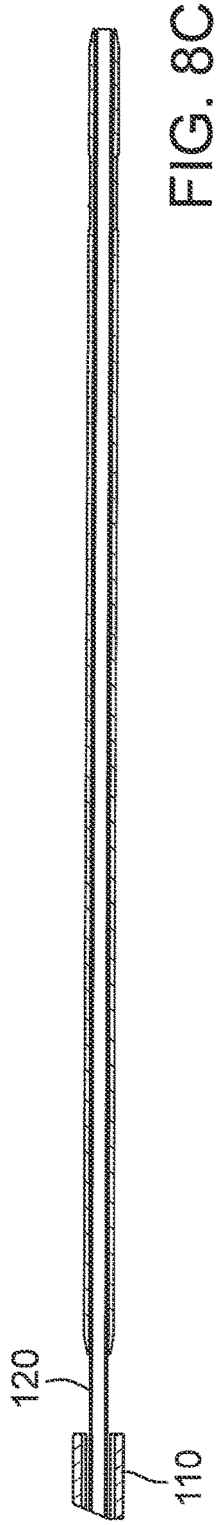

FIGS. 8 and 9 show a delivery apparatus 100, according to one embodiment, that can be used to deliver a self-expanding prosthetic valve, such as prosthetic valve 10 described above, through a patient's vasculature. The delivery apparatus 100 comprises a first, outermost or main catheter 102 (shown alone in FIG. 10) having an elongated shaft 104, the distal end of which is coupled to a delivery sheath 106 (FIG. 18; also referred to as a delivery cylinder). The proximal end of the main catheter 102 is connected to a handle of the delivery apparatus. FIGS. 23-26 show an embodiment of a handle mechanism having an electric motor for operating the delivery apparatus. The handle mechanism is described in detail below. During delivery of a prosthetic valve, the handle can be used by a surgeon to advance and retract the delivery apparatus through the patient's vasculature. Although not required, the main catheter 102 can comprise a guide catheter that is configured to allow a surgeon to guide or control the amount the bending or flexing of a distal portion of the shaft 104 as it is advanced through the patient's vasculature, such as further described below. Another embodiment of a guide catheter is disclosed in U.S. Patent Publication No. 2008/0065011, which is incorporated herein by reference.

As best shown in FIG. 9, the delivery apparatus 100 also includes a second, intermediate catheter 108 (also referred to herein as a torque shaft catheter) having an elongated shaft 110 (also referred to herein as a torque shaft) and an elongated screw 112 connected to the distal end of the shaft 110. The shaft 110 of the intermediate catheter 108 extends coaxially through the shaft 104 of the main catheter 102. The delivery apparatus 100 can also include a third, nose-cone catheter 118 having an elongated shaft 120 and a nose piece, or nose cone, 122 secured to the distal end portion of the shaft 120. The nose piece 122 can have a tapered outer surface as shown for atraumatic tracking through the patient's vasculature. The shaft 120 of the nose-cone catheter extends through the prosthetic valve 10 (not shown in FIGS. 8-9) and the shaft 110 of the intermediate catheter 108. In the illustrated configuration, the innermost shaft 120 is configured to be moveable axially and rotatably relative to the shafts 104, 110, and the torque shaft 110 is configured to be rotatable relative to the shafts 104, 120 to effect valve deployment and release of the prosthetic valve from the delivery apparatus, as described in detail below. Additionally, the innermost shaft 120 can have a lumen for receiving a guide wire so that the delivery apparatus can be advanced over the guide wire inside the patient's vasculature.

As best shown in FIG. 10, the outer catheter 102 can comprise a flex control mechanism 168 at a proximal end thereof to control the amount the bending or flexing of a distal portion of the outer shaft 104 as it is advanced through the patient's vasculature, such as further described below. The outer shaft 104 can comprise a proximal segment 166 that extends from the flex control mechanism 168 and a distal segment 126 that comprises a slotted metal tube that increases the flexibility of the outer shaft at this location. The distal end portion of the distal segment 126 can comprises an outer fork 130 of a valve-retaining mechanism 114 that is configured to releasably secure a prosthetic valve 10 to the delivery apparatus 100 during valve delivery, as described in detail below.

Figure 28A:
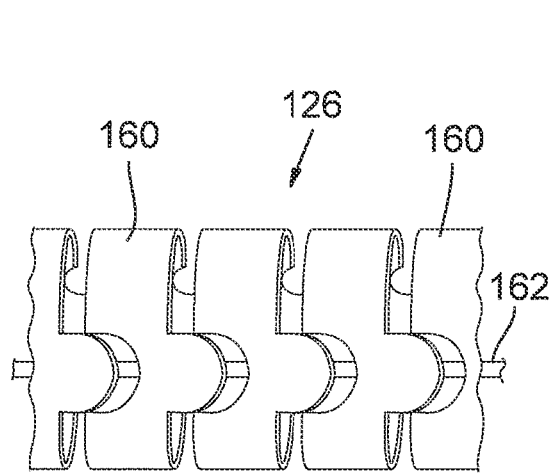
FIG. 28A is an enlarged view of a distal segment of the guide catheter shaft of FIG. 10.
Figure 28B:
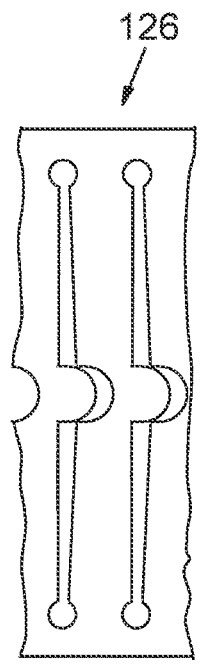
FIG. 28B shows the cut pattern for forming the portion of the shaft shown in FIG. 28A, such as by laser cutting a metal tube.

FIG. 28A is an enlarged view of a portion of the distal segment 126 of the outer shaft 104. FIG. 28B shows the cut pattern that can be used to form the distal segment 126 by laser cutting the pattern in a metal tube. The distal segment 126 comprises a plurality of interconnected circular bands or links 160 forming a slotted metal tube. A pull wire 162 can be positioned inside the distal segment 126 and can extend from a location 164 of the distal segment 126 (FIGS. 10 and 12) to the flex control mechanism 168. The distal end of the pull wire 162 can be secured to the inner surface of the distal segment 126 at location 164, such as by welding. The proximal end of the pull wire 162 can be operatively connected to the flex control mechanism 168, which is configured to apply and release tension to the pull wire in order to control bending of the shaft, as further described below. The links 160 of the shaft and the gaps between adjacent links are shaped to allow bending of the shaft upon application of light pulling force on the pull wire 162. In the illustrated embodiment, as best shown in FIG. 12, the distal segment 126 is secured to a proximal segment 166 having a different construction (e.g., one or more layers of polymeric tubing). In the illustrated embodiment, the proximal segment 166 extends from the flex control mechanism 168 to the distal segment 126 and therefore makes up the majority of the length of the outer shaft 104. In alternative embodiments, the entire length or substantially the entire length of the outer shaft 104 can be formed from a slotted metal tube comprising one or more sections of interconnected links 160. In any case, the use of a main shaft having such a construction can allow the delivery apparatus to be highly steerable, especially when use in combination with a torque shaft having the construction shown in FIGS. 13 and 14 (described below).

The width of the links 160 can be varied to vary the flexibility of the distal segment along its length. For example, the links within the distal end portion of the slotted tube can be relatively narrower to increase the flexibility of the shaft at that location while the links within the proximal end portion of the slotted tube can be relatively wider so that the shaft is relatively less flexible at that location.

Figure 29A:
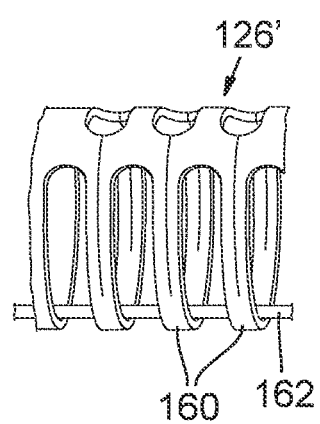
FIG. 29A is an enlarged view of a distal segment of a guide catheter shaft, according to another embodiment.
Figure 29B:
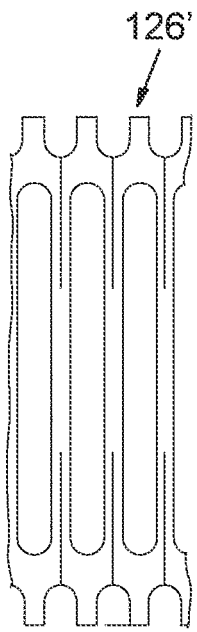
FIG. 29B shows the cut pattern for forming the shaft of FIG. 29A, such as by laser cutting a metal tube.

FIG. 29A shows an alternative embodiment of a distal segment, indicated at 126', which can be formed, for example, by laser cutting a metal tube. The segment 126' can comprise the distal segment of an outer shaft of a delivery apparatus (as shown in FIG. 12) or substantially the entire length of an outer shaft can have the construction shown in FIG. 29A. FIG. 29B shows the cut pattern for forming the segment 126'. In another embodiment, a delivery apparatus can include a composite outer shaft comprising a laser-cut metal tube laminated with a polymeric outer layer that is fused within the gaps in the metal layer. In one example, a composite shaft can comprise a laser cut metal tube having the cut pattern of FIGS. 29A and 29B and a polymeric outer layer fused in the gaps between the links 160 of the metal tube. In another example, a composite shaft can comprise a laser cut metal tube having the cut pattern of FIGS. 28A and 28B and a polymeric outer layer fused in the gaps between the links 160 of the metal tube. A composite shaft also can include a polymeric inner layer fused in the gaps between the links 160 of the metal tube.

Referring to FIGS. 8A and 11, the flex control mechanism 168 can comprise a rotatable housing, or handle portion, 186 that houses a slide nut 188 mounted on a rail 190. The slide nut 188 is prevented from rotating within the housing by one or more rods 192, each of which is partially disposed in a corresponding recess within the rail 190 and a slot or recess on the inside of the nut 188. The proximal end of the pull wire 162 is secured to the nut 188. The nut 188 has external threads that engage internal threads of the housing 186. Thus, rotating the housing 186 causes the nut 188 to move axially within the housing in the proximal or distal direction, depending on the direction of rotation of the housing. Rotating the housing 186 in a first direction (e.g., clockwise), causes the nut 188 to travel in the proximal direction, which applies tension to the pull wire 162, which causes the distal end of the delivery apparatus to bend or flex. Rotating the housing 186 in a second direction (e.g., counterclockwise), causes the nut 188 to travel in the distal direction, which relieves tension in the pull wire 162 and allows the distal end of the delivery apparatus to flex back to its pre-flexed configuration under its own resiliency.

As best shown in FIG. 13, the torque shaft catheter 108 includes an annular projection in the form of a ring 128 (also referred to as an anchoring disc) mounted on the distal end portion of the torque shaft 110 adjacent the screw 112. The ring 128 is secured to the outer surface of the torque shaft 110 such that it cannot move axially or rotationally relative to the torque shaft. The inner surface of the outer shaft 104 is formed with a feature, such as a slot or recess, that receives the ring 128 in such a manner that the ring and the corresponding feature on the inner surface of the outer shaft 104 allow the torque shaft 110 to rotate relative to the outer shaft 104 but prevent the torque shaft from moving axially relative to the outer shaft. The corresponding feature on the outer shaft 104 that receives the ring 128 can be inwardly extending tab portions formed in the distal segment 126, such as shown at 164 in FIG. 12. In the illustrated embodiment (as best shown in FIG. 14), the ring 128 is an integral part of the screw 112 (i.e., the screw 112 and the ring 128 are portions of single component). Alternatively, the screw 112 and the ring are separately formed components but are both fixedly secured to the distal end of the torque shaft 110.

The torque shaft 110 desirably is configured to be rotatable relative to the delivery sheath 106 to effect incremental and controlled advancement of the prosthetic valve 10 from the delivery sheath 106. To such ends, and according to one embodiment, the delivery apparatus 100 can include a sheath retaining ring in the form of a threaded nut 150 mounted on the external threads of the screw 112. As best shown in FIG. 16, the nut 150 includes internal threads 152 that engage the external threads of the screw 112 and axially extending legs 154. Each leg 154 has a raised distal end portion that extends into and/or forms a snap fit connection with openings 172 in the proximal end of the sheath 106 (as best shown in FIG. 18) so as to secure the sheath 106 to the nut 150. As illustrated in FIGS. 17B and 18, the sheath 106 extends over the prosthetic valve 10 and retains the prosthetic valve in a radially compressed state until the sheath 106 is retracted by the user to deploy the prosthetic valve.

Figure 21:
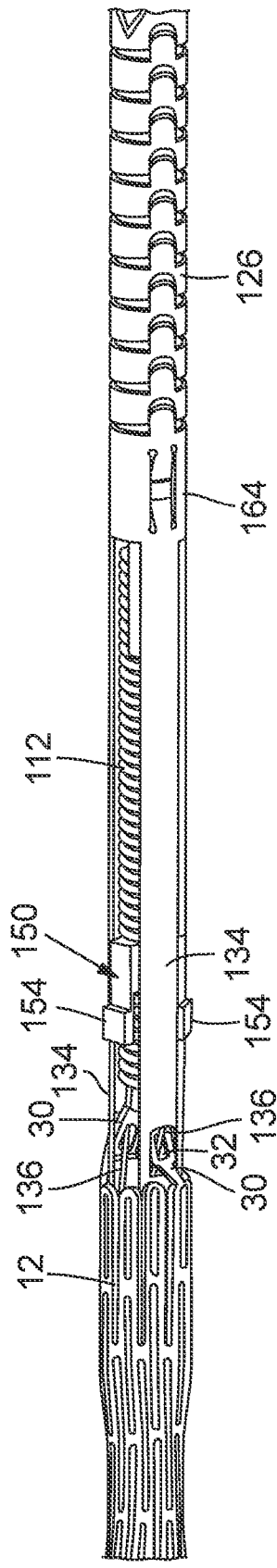
FIGS. 21 and 22 are enlarged side views of the distal end portion of the delivery apparatus of FIG. 8, illustrating the operation of the torque shaft for deploying a prosthetic valve from a delivery sheath.
Figure 22:
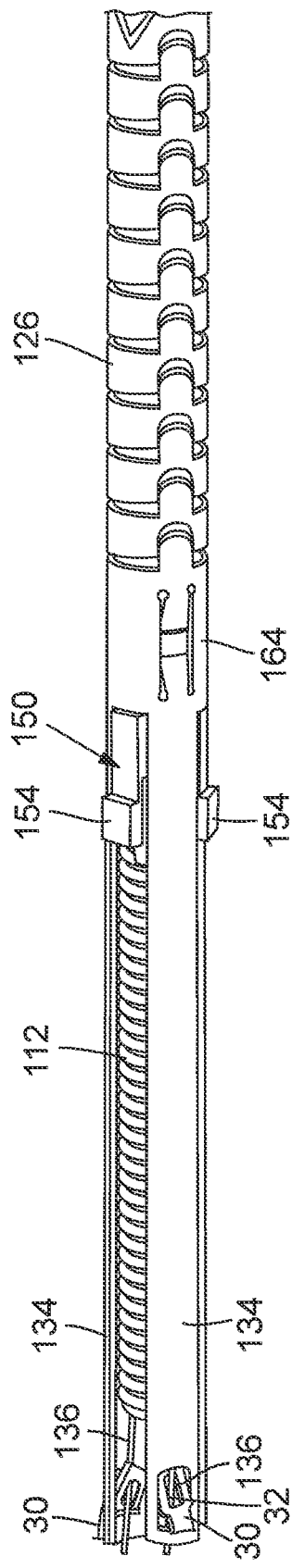

As best shown in FIGS. 21 and 22, the outer fork 130 of the valve-retaining mechanism comprises a plurality of prongs 134, each of which extends through a region defined between two adjacent legs 154 of the nut so as to prevent rotation of the nut relative to the screw 112 upon rotation of the screw. As such, rotation of the torque shaft 110 (and thus the screw 112) causes corresponding axial movement of the nut 150. The connection between the nut 150 and the sheath 106 is configured such that axially movement of the nut along the screw 112 (in the distal or proximal direction) causes the sheath 106 to move axially in the same direction relative to the screw and the valve-retaining mechanism. FIG. 21 shows the nut 150 in a distal position wherein the sheath 106 (not shown in FIG. 21) extends over and retains the prosthetic valve 10 in a compressed state for delivery. Movement of the nut 150 from the distal position (FIG. 21) to a proximal position (FIG. 22) causes the sheath 106 to move in the proximal direction, thereby deploying the prosthetic valve from the sheath 106. Rotation of the torque shaft 110 to effect axial movement of the sheath 106 can be accomplished with a motorized mechanism (such as shown in FIGS. 23-26 and described below) or by manually turning a crank or wheel.

Figure 17:
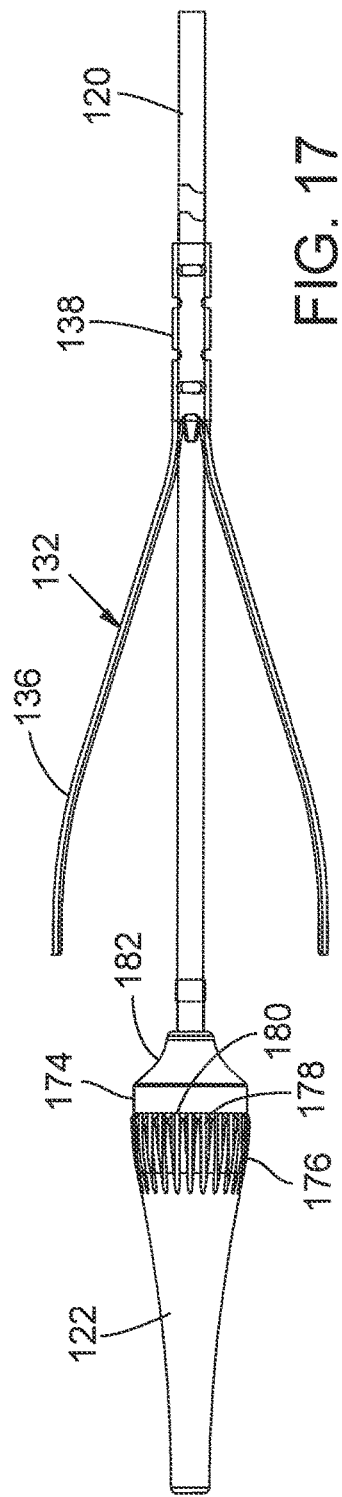
FIG. 17 is an enlarged side view of the distal end portion of the nose cone catheter of the delivery apparatus of FIG. 8.
Figure 17B:
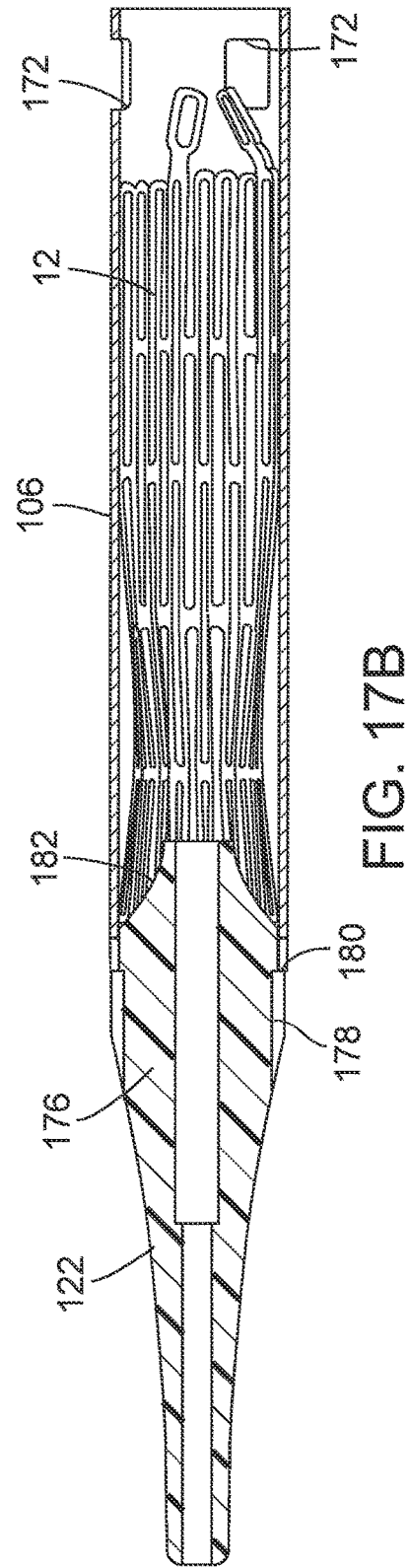
FIG. 17B is an enlarged cross-sectional view of the distal end portion of the delivery apparatus of FIG. 8 showing the stent of a prosthetic valve retained in a compressed state within a delivery sheath.
Figure 17A:
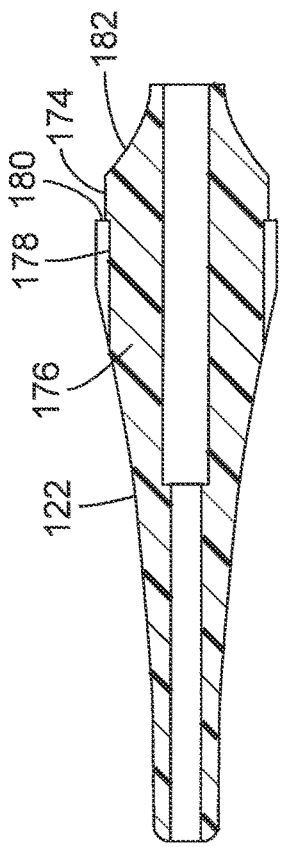
FIG. 17A is an enlarged, cross-sectional view of the nose cone of the catheter shown FIG. 17.

FIG. 17 shows an enlarged view of the nose cone 122 secured to the distal end of the innermost shaft 120. The nose cone 122 in the illustrated embodiment includes a proximal end portion 174 that is sized to fit inside the distal end of the sheath 106. An intermediate section 176 of the nose cone 122 is positioned immediately adjacent the end of the sheath 106 in use and is formed with a plurality of longitudinal grooves, or recessed portions, 178. The diameter of the intermediate section 176 at its proximal end 180 desirably is slightly larger than the outer diameter of the sheath 106. The proximal end 180 can be held in close contact with the distal end of the sheath 106 to protect surrounding tissue from coming into contact with the metal edge of the sheath. The grooves 178 allow the intermediate section 176 to be compressed radially as the delivery apparatus is advanced through an introducer sheath. This allows the nose cone 122 to be slightly oversized relative to the inner diameter of the introducer sheath. FIG. 17B shows a cross-section the nose cone 122 and the sheath 106 in a delivery position with the prosthetic valve retained in a compressed delivery state inside the sheath 106 (for purposes of illustration, only the stent 12 of the prosthetic valve is shown). As shown, the proximal end 180 of the intermediate section 176 can abut the distal end of the sheath 106 and a tapered proximal surface 182 of the nose cone 122 can extend within a distal portion of the stent 12.

As noted above, the delivery apparatus 100 can include a valve-retaining mechanism 114 (FIG. 8B) for releasably retaining a stent 12 of a prosthetic valve. The valve-retaining mechanism 114 can include a first valve-securement component in the form of an outer fork 130 (as best shown in FIG. 12) (also referred to as an "outer trident" or "release trident"), and a second valve-securement component in the form of an inner fork 132 (as best shown in FIG. 17) (also referred to as an "inner trident" or "locking trident"). The outer fork 130 cooperates with the inner fork 132 to form a releasable connection with the retaining arms 30 of the stent 12.

The proximal end of the outer fork 130 is connected to the distal segment 126 of the outer shaft 104 and the distal end of the outer fork is releasably connected to the stent 12. In the illustrated embodiment, the outer fork 130 and the distal segment 126 can be integrally formed as a single component (e.g., the outer fork and the distal segment can be laser cut or otherwise machined from a single piece of metal tubing), although these components can be separately formed and subsequently connected to each other. The inner fork 132 can be mounted on the nose catheter shaft 120 (as best shown in FIG. 17). The inner fork 132 connects the stent 12 to the distal end portion of the nose catheter shaft 120. The nose catheter shaft 120 can be moved axially relative to the outer shaft 104 to release the prosthetic valve 10 from the valve-retaining mechanism, as further described below.

As best shown in FIG. 12, the outer fork 130 includes a plurality of angularly-spaced prongs 134 (three in the illustrated embodiment) corresponding to the retaining arms 30 of the stent 12, which prongs extend from the distal end of distal segment 126. The distal end portion of each prong 134 includes a respective opening 140. As best shown in FIG. 17, the inner fork 132 includes a plurality of angularly-spaced prongs 136 (three in the illustrated embodiment) corresponding to the retaining arms 30 of the stent 12, which prongs extend from a base portion 138 at the proximal end of the inner fork. The base portion 138 of the inner fork 132 is fixedly secured to the nose catheter shaft 120 (e.g., with a suitable adhesive) to prevent axial and rotational movement of the inner fork relative to the nose catheter shaft 120.

Each prong 134 of the outer fork 130 cooperates with a corresponding prong 136 of the inner fork 132 to form a releasable connection with a retaining arm 30 of the stent 12. In the illustrated embodiment, for example, the distal end portion of each prong 134 is formed with an opening 140. When the prosthetic valve 10 is secured to the delivery apparatus (as best shown in FIG. 19), each retaining arm 30 of the stent 12 extends inwardly through an opening 140 of a prong 134 of the outer fork 130 and a prong 136 of the inner fork 132 is inserted through the opening 32 of the retaining arm 30 so as to retain the retaining arm 30 from backing out of the opening 140. Retracting the inner prongs 136 proximally (in the direction of arrow 184 in FIG. 20) to remove the prongs from the openings 32 is effective to release the prosthetic valve 10 from the retaining mechanism. When the inner fork 132 is moved to a proximal position (FIG. 20), the retaining arms 30 of the stent 12 can move radially outwardly from the openings 140 in the outer fork 130 under the resiliency of the stent. In this manner, the valve-retaining mechanism 114 forms a releasable connection with the prosthetic valve 10 that is secure enough to retain the prosthetic valve relative to the delivery apparatus 100 to allow the user to fine tune or adjust the position of the prosthetic valve after it is deployed from the delivery sheath. When the prosthetic valve 10 is positioned at the desired implantation site, the connection between the prosthetic valve and the retaining mechanism 114 can be released by retracting the nose catheter shaft 120 relative to the outer shaft 104 (which retracts the inner fork 132 relative to the outer fork 130).

Techniques for compressing and loading the prosthetic valve 10 into the sheath 106 are described below. Once the prosthetic valve 10 is loaded in the delivery sheath 106, the delivery apparatus 100 can be inserted into the patient's body for delivery of the prosthetic valve. In one approach, the prosthetic valve 10 can be delivered in a retrograde procedure where delivery apparatus is inserted into a femoral artery and advanced through the patient's vasculature to the heart. Prior to insertion of the delivery apparatus, an introducer sheath can be inserted into the femoral artery followed by a guide wire, which is advanced through the patient's vasculature through the aorta and into the left ventricle. The delivery apparatus 100 can then be inserted through the introducer sheath and advanced over the guide wire until the distal end portion of the delivery apparatus containing the prosthetic valve 10 is advanced to a location adjacent to or within the native aortic valve.

Thereafter, the prosthetic valve 10 can be deployed from the delivery apparatus 100 by rotating the torque shaft 110 relative to the outer shaft 104. As described below, the proximal end of the torque shaft 110 can be operatively connected to a manually rotatable handle portion or a motorized mechanism that allows the surgeon to effect rotation of the torque shaft 110 relative to the outer shaft 104. Rotation of the torque shaft 110 and the screw 112 causes the nut 150 and the sheath 106 to move in the proximal direction toward the outer shaft (FIG. 22), which deploys the prosthetic valve 10 from the sheath 106. Rotation of the torque shaft 110 causes the sheath 106 to move relative to the prosthetic valve 10 in a precise and controlled manner as the prosthetic valve advances from the open distal end of the delivery sheath and begins to expand. Hence, unlike known delivery apparatuses, as the prosthetic valve 10 begins to advance from the delivery sheath 106 and expand, the prosthetic valve is held against uncontrolled movement from the sheath caused by the expansion force of the prosthetic valve against the distal end of the sheath. In addition, as the sheath 106 is retracted, the prosthetic valve 10 is retained in a stationary position relative to the ends of the inner shaft 120 and the outer shaft 104 by virtue of the valve-retaining mechanism 114. As such, the prosthetic valve 10 can be held stationary relative to the target location in the body as the sheath 106 is retracted. Moreover, after the prosthetic valve 10 is partially advanced from the sheath 106, it may be desirable to retract the prosthetic valve back into the sheath, for example, to reposition the prosthetic valve or to withdraw the prosthetic valve entirely from the body. The partially deployed prosthetic valve 10 can be retracted back into the sheath 106 by reversing the rotation of the torque shaft 110, which causes the sheath 106 to advance back over the prosthetic valve in the distal direction.

In known delivery devices, the surgeon must apply push-pull forces to the shaft and/or the sheath to unsheathe the prosthetic valve. It is therefore difficult to transmit forces to the distal end of the device without distorting the shaft (e.g., compressing or stretching the shaft axially), which in turn causes uncontrolled movement of the prosthetic valve during the unsheathing process. To mitigate this effect, the shaft and/or sheath can be made more rigid, which is undesirable because the device becomes harder to steer through the vasculature. In contrast, the manner of unsheathing the prosthetic valve described above eliminates the application of push-pull forces on the shaft, as required in known devices, so that relatively high and accurate forces can be applied to the distal end of the shaft without compromising the flexibility of the device. In certain embodiments, as much as 20 lbs. of force can be transmitted to the end of the torque shaft without adversely affecting the unsheathing process. In contrast, prior art devices utilizing push-pull mechanisms typically cannot exceed about 5 lbs. of force during the unsheathing process.

After the prosthetic valve 10 is advanced from the delivery sheath 106 and expands to its functional size, the prosthetic valve remains connected to the delivery apparatus via the retaining mechanism 114. Consequently, after the prosthetic valve 10 is advanced from the delivery sheath 106, the surgeon can reposition the prosthetic valve relative to the desired implantation position in the native valve such as by moving the delivery apparatus in the proximal and distal directions or side to side, or rotating the delivery apparatus, which causes corresponding movement of the prosthetic valve. The retaining mechanism 114 desirably provides a connection between the prosthetic valve 10 and the delivery apparatus 100 that is secure and rigid enough to retain the position of the prosthetic valve relative to the delivery apparatus against the flow of the blood as the position of the prosthetic valve is adjusted relative to the desired implantation position in the native valve. Once the surgeon positions the prosthetic valve 10 at the desired implantation position in the native valve, the connection between the prosthetic valve and the delivery apparatus 100 can be released by retracting the innermost shaft 120 in the proximal direction relative to the outer shaft 104, which is effective to retract the inner fork 132 to withdraw its prongs 136 from the openings 32 in the retaining arms 30 of the prosthetic valve (FIG. 20). Slightly retracting of the outer shaft 104 allows the outer fork 130 to back off the retaining arms 30 of the prosthetic valve 10, which slide outwardly through openings 140 in the outer fork to completely disconnect the prosthetic valve from the retaining mechanism 114. Thereafter, the delivery apparatus 100 can be withdrawn from the body, leaving the prosthetic aortic valve 10 implanted within the native valve (such as shown in FIGS. 5A and 5B).

The delivery apparatus 100 has at its distal end a semi-rigid segment comprised of relatively rigid components used to transform rotation of the torque shaft 110 into axial movement of the sheath 106. In particular, this semi-rigid segment in the illustrated embodiment is comprised of the prosthetic valve 10 and the screw 112. An advantage of the delivery apparatus 100 is that the overall length of the semi-rigid segment is minimized because the nut 150 is used rather than internal threads on the outer shaft to affect translation of the sheath 106. The reduced length of the semi-rigid segment increases the overall flexibility along the distal end portion of the delivery catheter. Moreover, the length and location of the semi-rigid segment remains constant because the torque shaft 110 does not translate axially relative to the outer shaft 104. As such, the curved shape of the delivery catheter can be maintained during valve deployment, which improves the stability of the deployment. A further benefit of the delivery apparatus 100 is that the ring 128 prevents the transfer of axial loads (compression and tension) to the section of the torque shaft 110 that is distal to the ring.

In an alternative embodiment, the delivery apparatus 100 can be adapted to deliver a balloon-expandable prosthetic valve. As described above, the valve retaining mechanism 114 can be used to secure the prosthetic valve to the end of the delivery apparatus 100. Since the stent of the prosthetic valve is not self-expanding, the sheath 106 can be optional. The retaining mechanism 114 enhances the pushability of the delivery apparatus 100 and prosthetic valve assembly through an introducer sheath.

FIGS. 23-26 illustrate the proximal end portion of the delivery apparatus 100, according to one embodiment. The delivery apparatus 100 can comprise a handle 202 that is configured to be releasably connectable to the proximal end portion of a catheter assembly 204 comprising catheters 102, 108, 118. It may be desirable to disconnect the handle 202 from the catheter assembly 204 for various reasons. For example, disconnecting the handle 202 can allow another device to be slid over the catheter assembly 204, such as a valve-retrieval device or a device to assist in steering the catheter assembly. It should be noted that any of the features of the handle 202 and the catheter assembly 204 can be implemented in any of the embodiments of the delivery apparatuses disclosed herein.

FIGS. 23 and 24 show the proximal end portion of the catheter assembly 204 partially inserted into a distal opening of the handle 202. The proximal end portion of the main shaft 104 is formed with an annular groove 212 (as best shown in FIG. 24) that cooperates with a holding mechanism, or latch mechanism, 214 inside the handle. When the proximal end portion of the catheter assembly is fully inserted into the handle 202, as shown in FIGS. 25 and 26, an engaging portion 216 of the holding mechanism 214 extends at least partially into the groove 212. One side of the holding mechanism 214 is connected to a button 218 that extends through the housing of the handle 202. The opposite side of the holding mechanism 214 is contacted by a spring 220 that biases the holding mechanism to a position engaging the main shaft 104 at the groove 212. The engagement of the holding mechanism 214 within the groove 212 prevents axial separation of the catheter assembly from the handle 202. The catheter assembly 204 can be released from the handle 202 by depressing button 218, which moves the holding mechanism 214 from locking engagement with the main shaft 104. Furthermore, the main shaft 104 can be formed with a flat surface portion within the groove 212. The flat surface portion is positioned against a corresponding flat surface portion of the engaging portion 216. This engagement holds the main shaft 104 stationary relative to the torque shaft 110 as the torque shaft is rotated during valve deployment.

The proximal end portion of the torque shaft 110 can have a driven nut 222 (FIG. 26) that is slidably received in a drive cylinder 224 (FIG. 25) mounted inside the handle 202. The nut 222 can be secured to the proximal end of the torque shaft 100 by securing the nut 222 over a coupling member 170 (FIG. 15). FIG. 26 is a perspective view of the inside of the handle 202 with the drive cylinder 224 and other components removed to show the driven nut 222 and other components positioned within the drive cylinder. The cylinder 224 has a through opening (or lumen) extending the length of the cylinder that is shaped to correspond to the flats of the nut 222 such that rotation of the drive cylinder is effective to rotate the nut 222 and the torque shaft 110. The drive cylinder 224 can have an enlarged distal end portion 236 that can house one or more seals (e.g., O-rings 246) that form a seal with the outer surface of the main shaft 104 (FIG. 25). The handle 202 can also house a fitting 238 that has a flush port in communication with the lumen of the torque shaft and/or the lumen of the main shaft 104.

The drive cylinder 224 is operatively connected to an electric motor 226 through gears 228 and 230. The handle 202 can also house a battery compartment 232 that contains batteries for powering the motor 226. Rotation of the motor 226 in one direction causes the torque shaft 110 to rotate, which in turn causes the sheath 106 to retract and uncover a prosthetic valve at the distal end of the catheter assembly. Rotation of the motor 226 in the opposite direction causes the torque shaft 110 to rotate in an opposite direction, which causes the sheath 106 to move back over the prosthetic valve. An operator button 234 on the handle 202 allows a user to activate the motor, which can be rotated in either direction to un-sheath a prosthetic valve or retrieve an expanded or partially expanded prosthetic valve.

As described above, the distal end portion of the nose catheter shaft 120 can be secured to an inner fork 132 that is moved relative to an outer fork 130 to release a prosthetic valve 10 secured to the end of the delivery apparatus 100. Movement of the shaft 120 relative to the main shaft 104 (which secures the outer fork 130) can be effected by a proximal end portion 240 of the handle 202 that is slidable relative to the main housing 244. The end portion 240 is operatively connected to the shaft 120 such that movement of the end portion 240 is effective to translate the shaft 120 axially relative to the main shaft 104 (causing a prosthetic valve 10 to be released from the inner 132 and outer 130 forks). The end portion 240 can have flexible side panels 242 on opposite sides of the handle 202 that are normally biased outwardly in a locked position to retain the end portion relative to the main housing 244. During deployment of the prosthetic valve, the user can depress the side panels 242, which disengage from corresponding features in the housing and allow the end portion 240 to be pulled proximally relative to the main housing, which causes corresponding axial movement of the shaft 120 relative to the main shaft 104. Proximal movement of the shaft 120 causes the prongs 136 of the inner fork 132 to disengage from the apertures 32 in the stent 12, which in turn allows the retaining arms 30 of the stent to deflect radially outwardly from the openings 140 in the prongs 134 of the outer fork 130, thereby releasing the prosthetic valve.

FIG. 27 shows an alternative embodiment of a motor, indicated at 400, that can be used to drive a torque shaft (e.g., torque shaft 110). In this embodiment, a catheter assembly can be connected directly to one end of a shaft 402 of the motor, without gearing. The shaft 402 includes a lumen that allows for passage of an innermost shaft (e.g., shaft 120) of the catheter assembly, a guide wire, and/or fluids for flushing the lumens of the catheter assembly.

Alternatively, the power source for rotating the torque shaft 110 can be a hydraulic power source (e.g., hydraulic pump) or pneumatic (air-operated) power source that is configured to rotate the torque shaft. In another embodiment, the handle 202 can have a manually movable lever or wheel that is operable to rotate the torque shaft 110.

In another embodiment, a power source (e.g., an electric, hydraulic, or pneumatic power source) can be operatively connected to a shaft, which is turn is connected to a prosthetic valve 10. The power source is configured to reciprocate the shaft longitudinally in the distal direction relative to a valve sheath in a precise and controlled manner in order to advance the prosthetic valve from the sheath. Alternatively, the power source can be operatively connected to the sheath in order to reciprocate the sheath longitudinally in the proximal direction relative to the prosthetic valve to deploy the prosthetic valve from the sheath.

Figure 30:
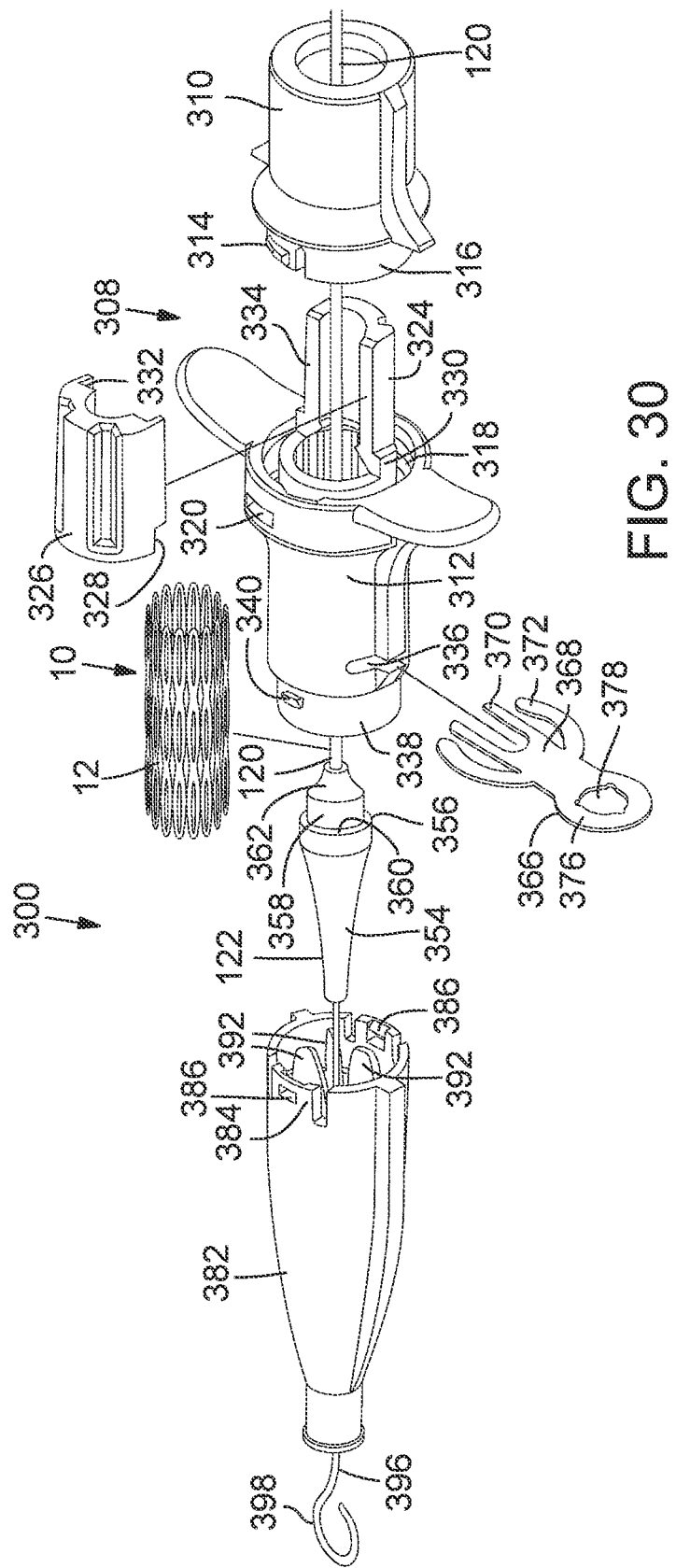
FIG. 30 is an exploded view of a valve storage assembly useable with the delivery apparatus of FIG. 8.

FIGS. 30 and 31 present, respectively, an exploded view and a cross-sectional view of a valve storage assembly 300 that may be used in at least certain embodiments of the present disclosure for storing a prosthetic valve prior to use. The valve storage assembly 300 in the illustrated embodiment includes a storage tube assembly 308, a retaining tab 366, and a nose cone cap 382. The storage tube assembly 308 may be used to store the prosthetic valve 10, such as in a partially crimped state, until the valve 10 is ready to be implanted in a patient.

The storage tube assembly 308 can include a proximal storage tube portion 310 and a distal storage tube portion 312. The proximal storage tube portion 310 can include locking tabs 314 that extend radially from opposing sides of an axially extending annular lip 316 formed at the distal end of the proximal storage tube portion 310. The proximal end of the distal storage tube portion 312 can define a circumferentially extending, annular recess 318 formed between an outer wall and an inner lip portion of the distal storage tube portion 312. The outer surface of the distal storage tube portion 312 can define slots 320 at opposing points, the slots providing an opening into the circumferential recess 318.

The distal storage tube portion 312 can include an extension portion 324 configured to receive a cap portion 326. For example, the cap portion 326 may include notches 328 to be received by mating ridges 330 formed in the surface of the extension portion 324. The cap portion 326 can further include a lip 332 extending from the notches 328 to the proximal end of the cap portion 326. The lip 332 can be configured to engage the upper surface 334 of the extension portion 324, which has a width smaller than the width of the cap portion 326 between the opposing sides of the lip 332. Opposing sides of the distal end of the distal storage tube portion 312 can include tab slots 336. A reduced diameter lip 338 extends from the distal end of the distal storage tube portion 312 and can include radially extending locking tabs 340.

During assembly of the storage tube assembly 308, the cap portion 326 is secured to the extension portion 324. The proximal 310 and distal 312 storage tube portions are coupled to each other by inserting the lip 316 and tabs 314 of the proximal storage tube portion 310 into the corresponding recess 318 and slots 320 of the distal storage tube portion 312, as shown in FIG. 31. The proximal storage tube portion 310 fits over the cap portion 326 and holds it in place on the extension portion 324.

With reference to FIG. 31, the sheath 106 can extend through the proximal end of the proximal portion 310 of the storage tube assembly 308. As shown, the inner surfaces of the extension portion 324 and the cap portion 326 of the distal storage tube portion 312 provide a tapered surface 344 extending from an inner bore 346 containing the valve 10 to a reduced diameter inner bore 348 housing the sheath 106. The tapered surface 344 helps guide and fully crimp the prosthetic valve 10 as it is pulled within the sheath 106. The opening of the bore 348 closest to the tapered surface 344 can be formed with an annular lip 350 that abuts the distal end of the sheath 106.

Referring again to FIG. 30, the shaft 120 of the nose cone catheter 118 extends through the storage tube assembly 308 through an opening in the proximal end of the proximal storage tube portion 310. The nose cone 122 can include a distal, conical portion 354 that extends from the distal apex to a base 356. An intermediate nose cone portion 358 can extend proximally from the base 356. The diameter of the intermediate nose cone portion 358 can be smaller than the diameter of the distal portion 354 at its base 356. The proximal, annular surface of the base 356 extending about the intermediate nose cone portion 358 forms a shelf 360. In some implementations, the intermediate nose cone portion 358 has a constant diameter. In other implementations, the intermediate nose cone portion 358 is tapered, such as having a diameter that reduces towards the proximal end of the nose cone 122. The nose cone 122 can further include a tapered proximal section 362 that reduces in diameter, including compared with the diameter of the intermediate nose cone portion 358, towards the proximal end of the nose cone 122. The nose cone 122 is releasably retained in a fixed position relative to the storage tube assembly 308 using the retaining tab 366.

The retaining tab 366 can include a tab body 368 having flat distal and proximal faces. One end portion of the tab body 368 comprises a pair of inner arms 370. The fixed ends of the inner arms 370 can form an arcuate surface at their juncture with an intermediate section of the tab body 368. For example, the inner arms 370 may be in the form of a partial obround. The tab body 368 can further include a pair of arcuate outer arms 372 extending away from the intermediate section of the tab body 368. Thus, the inner arms 370 are disposed within the outer arms 372. The end portion of the tab body 368 opposite the arms can comprise a disk-shaped extension 376, which can define an aperture 378.

During assembly, the tab 366 is secured to the nose cone 122 by inserting the inner arms 370 of the tab 366 through the tab slots 336 of the distal storage tube portion 312 and about the intermediate portion 358 of the nose cone 122. The tab 366 may be placed such that the distal face of the tab 366 abuts the shelf 360 of the nose cone 122. As best shown in FIG. 31, the outer arms 372 of the tab 366 extend about and engage the outer radial surface of the distal tube portion 312. The outer arms 372 are sufficiently flexible to flex outwardly away from the inner arms 370, as the outer arms are forced over the outer surface of the distal tube portion 312. Once the tab 366 is inserted into the distal storage tube portion 312, the outer arm 372 can be biased against the outer surface of the distal storage tube to assist in retaining the tab 366 in place until removed by the physician.

In other implementations, the tab 366 is configured differently than shown in FIG. 30. For example, the tab 366 may lack the outer arms 372. In such implementations, the tab 366 may be retained in the proper position between the nose cone 122 and the frame 12 by other means. For example, the inner arms 370 may be shaped or dimensioned to more securely engage the intermediate nose cone portion 358, such as by narrowing the gap between the inner arms 370. In another example, the tab 366 is maintained in position by compressing the tab 366 between the intermediate nose cone portion 358 and the frame 12 of the valve 10, such as by a nose cone cap 382 (described further below), which may be secured to the storage tube assembly 308.

The tab 366 prevents movement of the nose cone catheter 118 (including its shaft 120) in the proximal direction relative to the prosthetic valve 10 and the sheath 106 during shipping and subsequent handling by the physician in the operating room prior to insertion into a patient. The tab 366 also sets the distance between the distal end of the sheath 106 and the shelf 360 of the nose cone 122. During loading of the prosthetic valve 10 into the sheath 106, the prosthetic valve 10 can, depending on the construction of the frame 12, expand lengthwise as it is compressed radially. The thickness of the tab 366 desirably is selected to accommodate lengthwise expansion of the frame 12 such that when the prosthetic valve 10 is fully loaded into the sheath 106, the distal end of the sheath 106 can abut the shelf 360 of the nose cone 122. In the loaded configuration, the sheath 106 completely encloses the prosthetic valve 10 and protects against direct contact between the distal end of the frame 12 and surrounding tissue as the delivery apparatus is advanced through the patient's vasculature. Also, in some embodiments, it may be desirable to flush the leaflets 34a, 34b, 34c with saline or another liquid prior to implantation. After loading the prosthetic valve, saline or another liquid can be injected into the sheath 106. The sheath 106 can form a seal with the nose cone 122 sufficient to maintain the liquid in the sheath during the flushing step.

Different tab thicknesses may be selected depending on factors such as the shape and size of the nose cone 122, the shape, size, and diameter of the frame 12, and the amount of expansion experienced by the frame 12 when it is withdrawn into the sheath 106. In specific implementations, the thickness of at least a portion of the tab 366, such as the inner arms 370, is between about 0.005 inches and about 0.1 inches, such as between about 0.010 inches and about 0.075 inches, or between about 0.02 inches and about 0.04 inches. In further implementations, the thickness is about 0.025 inches or about 0.031 inches, such as being 0.025 inches or 0.031 inches. In particular examples, a thickness being "about" a value means being the value or within 0.002 inches of the value, or being within a range of 10% higher or lower than the recited thickness.

The valve storage assembly 300 further includes the nose cone cap 382. The nose cone cap 382 is generally conical in the illustrated embodiment, extending from a distal apex to a proximal base portion. A pair of arms 384 can extend from the base and can include slots 386 for receiving the locking tabs 340 of the proximal storage tube portion 312. As best shown in FIG. 31, an axial bore 388 extends through the interior of the nose cone cap 382, including through the distal apex. As best shown in FIG. 32, the interior of the nose cone cap 382 can include a plurality of axial fins 392 extending radially into the interior of the nose cone cap 382. The fins 392 are tapered at their proximal and distal ends such that, combined with the diameter of the nose cone cap 382 tapering toward its distal apex, the fins 392 define a conical cavity within the interior of the nose cone cap 382, the cavity having an apex towards the distal end of the nose cone cap 382. In at least certain implementations, the fins 392 can extend slightly proximally beyond the proximal end of the nose cone cap 382, but not beyond the slots 386. The nose cone cap 382 prevents distal movement of the nose cone catheter 118 (including its shaft 120) relative to the prosthetic valve 10 and the sheath 106 during shipping and subsequent handling of the delivery apparatus 100 by the physician prior to insertion into a patient.

Referring back to FIGS. 30 and 31, a stylet 396 can be inserted through the distal end of the nose cone cap 382, through the nose cone 122 and the shaft 120 of the nose cone catheter 118. The stylet 396 can include a loop 398 at its distal end. The loop 398 is configured to have a diameter larger than the diameter of the opening of the axial bore 388 at the apex of the nose cone cap 382.

The nose cone cap 382 may have other configurations. In a particular implementation, the nose cone cap 382 includes a latch releasably coupled to a tether (not shown). The tether is coupled to the nose cone cap 382, such as extending through one or more apertures (not shown) formed in the nose cone cap 382. A component of the tether or latch, such as a pin, is configured to be inserted through the loop 398 of the stylet 396 and coupled to the tether. When coupled to the tether, the component, such as the pin, resists axial movement of the stylet 396.

During assembly, the nose cone cap 382 is placed over the nose cone 122 such that the distal portion 354 of the nose cone 122 is received in the conical cavity of the nose cone cap 382 formed by the fins 392. The slots 386 of the arms 384 are urged over the locking tabs 340 of the distal storage tube portion 312, such that the nose cone cap 382 is secured to the storage tube assembly 308, with the nose cone 122 being secured between, and relative to, the nose cone cap and the storage tube assembly. The stylet 396 is inserted through the apex of the nose cap 382, the nose cone 122, and the shaft 118. The stylet 396 serves to protect the components through which it passes from being damaged, and in particular the shaft 118, such as by compressive or bending forces experienced by the components during assembly and packaging of the delivery apparatus 100, and during subsequent handling of the delivery apparatus prior to insertion into a patient.

In particular embodiments, an assembly that includes the delivery apparatus 100, the valve storage assembly 300, and the partially crimped prosthetic valve 10 (inside bore 346) can be packaged together in a sterile package enclosing all of these components. The package containing these components can be supplied to end users for storage and eventual use.

When the surgeon is ready to implant the prosthetic valve in a patient, the delivery apparatus 100, the partially crimped prosthetic valve 10, and the valve storage assembly 300 can be removed from the package while inside the operating room. When the end user is ready to implant the valve 10, the user may remove the nose cap 382 by releasing the locking tabs 340 from the slots 386. The user may then remove the tab 366 from engagement with the nose cone 122 and withdraw the tab 366 from the slot 336 in the distal storage tube portion 312. The prosthetic valve 10 can then be loaded into the sheath 106 and the stylet 396 can be removed from the delivery apparatus 100.

Figure 33:
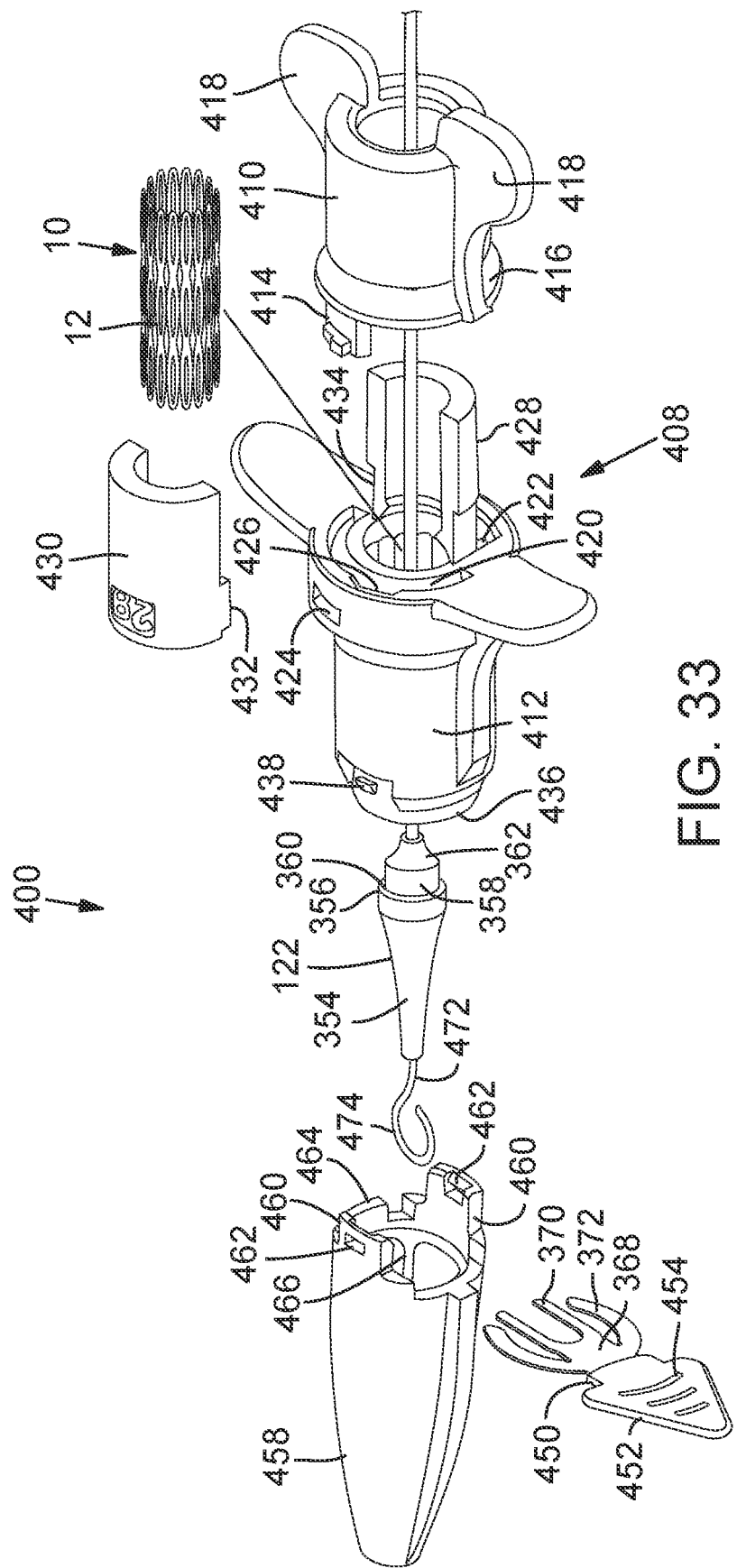
FIG. 33 is an exploded view of another implementation of a valve storage assembly useable with the delivery apparatus of FIG. 8.

FIGS. 33-35 present, respectively, an exploded view and cross-sectional views (taken through two different axes) of an alternative valve storage assembly 400 that may be used in at least certain embodiments of the present disclosure. The valve storage assembly 400 can include a storage tube assembly 408, a retaining tab 450, and a nose cone cap 458. The storage tube assembly 408 may be used to store the prosthetic valve 10, such as in a partially crimped state, until the valve 10 is ready to be implanted in a patient.

The storage tube assembly 408 can include a proximal storage tube portion 410 and a distal storage tube portion 412. The proximal storage tube portion 410 can include locking tabs 414 that extend radially from an axially extending annular lip 416 formed at the distal end of the proximal storage tube portion 410. The proximal end of the proximal storage tube portion 410 can include a pair of radially extending wings 418. The wings 418 can be generally arcuate, such as generally semi-circular.

The proximal end of the distal storage tube portion 412 can define upper and lower circumferential recesses 420, 422. The outer surface of the distal storage tube portion 412 can define slots 424 at opposing locations, the slots 424 providing openings into the circumferential recesses 420, 422. The upper and lower circumferential recesses 420, 422 can further define a pair of notches 426, where the recesses 420, 422 extend further towards the outer surface of the proximal end of the distal storage tube portion 412. The notches 426 can be slightly circumferentially offset with respect to the slots 424.

The distal storage tube portion 412 can include an extension portion 428 configured to receive a cap portion 430. For example, the cap portion 430 may include tabs 432 to be received by mating slots 434 formed in the surface of the extension portion 428. A reduced diameter lip 436 can extend axially from the distal end of the distal storage tube portion 412 and can include radially extending locking tabs 438.

During assembly of the storage tube assembly 408, the cap portion 430 can be placed on the extension portion 428 by inserting the tabs 432 into the slots 434. The proximal 410 and distal 412 storage tube portions are coupled together by inserting the locking tabs 414 of the distal storage tube portion 412 through the notches 426, and then rotating the proximal storage tube portion 410 such that the locking tabs 414 engage the slots 424 of the distal tube portion 412. The wings 418 can assist the user in grasping, inserting, and twisting the proximal storage tube portion 410 during this assembly process. The proximal storage tube portion 410 fits over the cap portion 430 and holds it in place against the extension portion 428.

As best shown in FIG. 35, the valve 10 is substantially retained within the bore 440 of the distal storage tube portion 412. The distal storage tube portion 412 can be sized such that the distal portion of the valve frame 12 extends slightly beyond the distal end of the distal storage tube portion 412.

The sheath 106 extends through the proximal end 410 of the storage tube assembly 408. As shown, the inner surfaces of the extension portion 428 and the cap portion 430 of the distal storage tube portion 412 can include a tapered surface 442 extending from the inner bore 440 containing the valve 10 to a reduced diameter inner bore 444 housing the sheath 106. The tapered surface 442 helps guide and fully crimp the prosthetic valve 10 as it is pulled within the sheath 106 during preparation of the device for use. The opening of the bore 444 closest to the tapered surface 442 can be formed with an annular lip 446 that abuts the distal end of the sheath 106.

The shaft 120 of the nose cone catheter 118 extends through the storage tube assembly 408 via an opening in the proximal end of the proximal storage tube portion 410. The nose cone 122 can be configured as described above with reference to FIGS. 30 and 31. The nose cone 122 can be releasably retained in position using the retaining tab 450.

Unless otherwise specified, the tab 450 can be generally configured in a similar manner as the tab 366 of FIGS. 30 and 31. However, rather than having a disk-shaped extension 376 with an aperture 378, the tab 450 can include a gripping portion 452. The gripping portion 452 can be thicker than the legs 370, 372. In a particular example, the gripping portion 452 can be formed by overmolding a plastic material over an end portion of the tab body 368.

As shown in FIG. 33, the gripping portion 452 can include a plurality of ridges 454 formed on the faces of the gripping portion 452. As shown, the gripping portion 452 can have a triangular shape, with an apex at the proximal end of the gripping portion 452. However, in other implementations, the gripping portion 452 has a different shape, or includes features other than, or in addition to, the ridges 454 to facilitate gripping. For example, the gripping portion 452 may be formed from a material with a high coefficient of friction, or from a resilient material.

In a specific example, the gripping portion 452 is formed from, or coated with, a colored material that helps attract attention to the gripping portion.

The valve storage assembly 400 can further include the nose cone cap 458. The nose cone cap 458 can be generally conical, extending from a distal apex to a proximal base portion. A pair of arms 460 can extend axially from the base and can include slots 462 for receiving the locking tabs 438 of the proximal storage tube portion 412. A shorter tab arm 464 can extend axially from the base. The width of the tab arm 464 is configured such that the inner arms 370 of the tab 450 may be disposed about the radial sides of the tab arm 464. The side of the base opposite the tab arm 464 provides a recess for receiving the tab 450.

Figure 36:
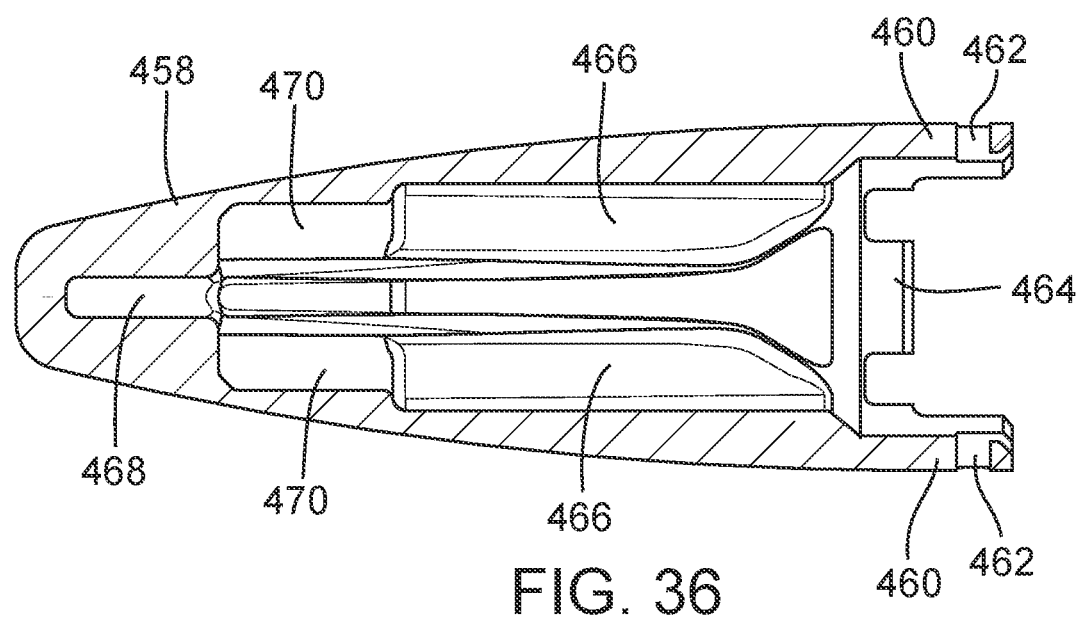
FIG. 36 is an enlarged cross-sectional view of a nose cone cap useable with the valve storage assembly of FIGS. 33-35.

As best shown in FIG. 36, the interior of the nose cone cap 458 include a plurality of axial fins 466 extending radially into the interior of the nose cone cap. The fins 466 are tapered at their proximal and distal ends such that, combined with the diameter of the nose cone cap 458 tapering toward its distal apex, the fins 466 define a conical cavity within the interior of the nose cone cap, the cavity having an apex towards the distal end of the nose cone cap. In at least certain implementations, the proximal ends of the fins 466 taper radially inwardly moving distally toward the base of the nose cone cap 458. An inner bore 468 extends proximally from the apex of the conical cavity formed by the fins 466. A recess or groove 470 can be formed within the nose cone cap 458, about a distal portion of the inner bore 468. As best shown in FIG. 35, the inner bore 468 can be configured to receive a stylet 472. A curved distal end 474 of the stylet 472 can be received by the recess 470.

With reference to FIGS. 33 and 35, during assembly, the inner arms 370 of the tab 450 are inserted about the intermediate portion 358 of the nose cone 122. A proximal face of the tab 450 can abut the portion of the valve frame 12 extending beyond the distal storage tube portion 412. The stylet 472 can be inserted through the nose cone 122 and the shaft 120. The nose cone cap 458 can be placed over the stylet 472 and the nose cone 122, such that the stylet 472 is received by the recess 470 of the nose cone cap 458, and the nose cone 122 is received within the conical cavity formed by the fins 466. The locking tabs 438 of the distal storage tube portion 412 are urged into engagement with the slots 462 of the nose cone cap arms 460. During attachment of the nose cone cap 458 to the storage tube assembly 408, the tab arm 464 is inserted through the inner arms 370 of the tab 450. The outer arms 372 of the tab 450 wrap around the outer surface of the nose cone cap 458, helping to secure the tab against inadvertent movement until a user desires to remove the tab.

In particular embodiments, an assembly comprising the delivery apparatus 100, the valve storage assembly 400, and the partially crimped prosthetic valve 10 (inside bore 440) can be packaged together in a sterile package enclosing all of these components. The package containing these components can be supplied to end users for storage and eventual use.

When the surgeon is ready to implant the prosthetic valve 10 in a patient, the delivery apparatus 100, the partially crimped prosthetic valve 10, and the valve storage assembly 400 can be removed from the package while inside the operating room. When the end user is ready to implant the valve 10, the user may remove the tab 450 from the nose cone 122 by grasping and pulling the gripping portion 452. The size and, optionally, color, or other features, of the tab 450 help remind the user to remove the tab 450 prior to using the delivery apparatus 100. The nose cone cap 458 may be removed by releasing the locking tabs 438 from the slots 462.

For both the valve storage assembly 300 and the valve storage assembly 400, with the nose cone 122 no longer secured, the user may load the prosthetic valve 10 into the sheath 106 by rotating the torque shaft 110 in a direction to urge the sheath 106 against the annular lip 350, 446, which causes the prosthetic valve 10 to slide into the sheath 106 (as best shown in FIG. 17B). If a motorized handle 202 is provided (as described above), the torque shaft 110 can be rotated by actuating the motor of the handle. Once the prosthetic valve 10 is inside the sheath 106, the storage tube assembly 308, 408 can be removed from the delivery apparatus 100, which is now ready for insertion into the patient. As can be appreciated, storing the prosthetic valve 10 in a partially crimped state inside the storage tube assembly eliminates the task of connecting the prosthetic valve to the delivery apparatus and greatly simplifies the crimping process for the surgeon.

In particular embodiments, the leaflets 34 of the prosthetic valve (typically made from bovine pericardium tissue or other natural or synthetic tissues) are treated during the manufacturing process so that they are completely or substantially dehydrated and can be stored in a partially or fully crimped state without a hydrating fluid. In this manner, the package containing the prosthetic valve and the delivery apparatus can be free of any liquid. Methods for treating tissue leaflets for dry storage are disclosed in U.S. Pat. No. 8,007,992 and U.S. Patent Publication No. 2009/0164005, filed Dec. 18, 2008, both of which documents are incorporated herein by reference. In addition, additional details regarding the loading of the valve 10 within a storage tube are described in U.S. Patent Publication No. 2012/0239142 (application Ser. No. 13/405,119), filed Feb. 24, 2012, incorporated by reference herein.

Figure 37:
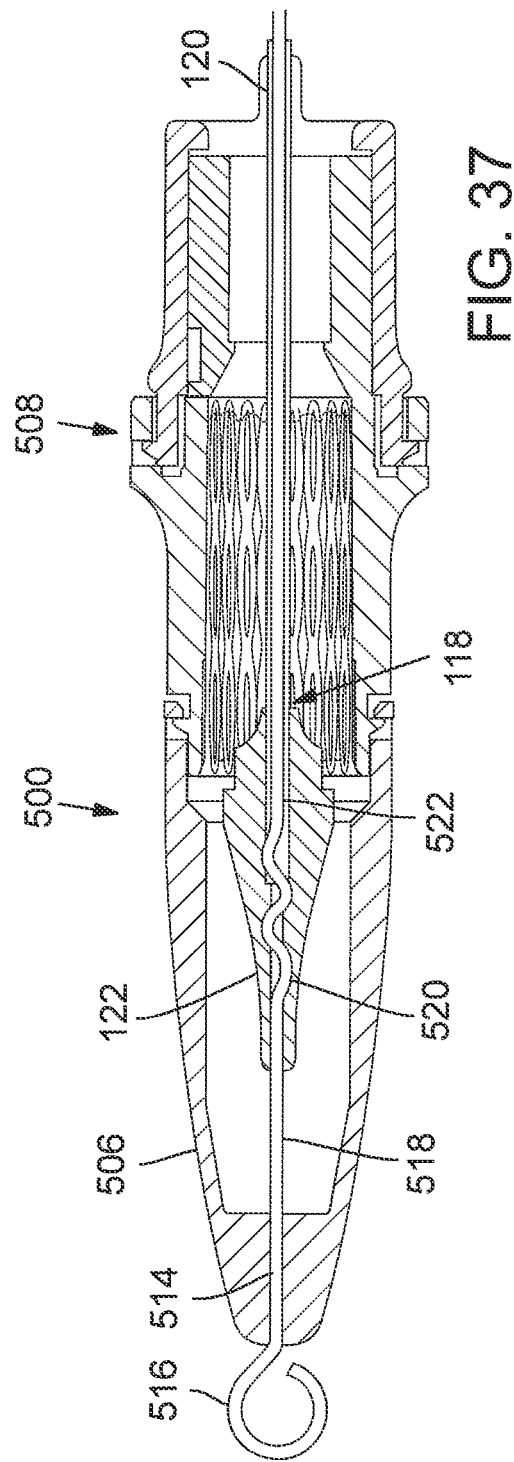
FIG. 37 is a cross-sectional view of an alternative valve storage assembly useable with the delivery assembly of FIG. 8, having a stylet incorporating one or more bends.

FIG. 37 illustrates a valve storage assembly 500 that may be used to help maintain the nose cone 122 in a fixed axial position relative to the prosthetic valve 10 and the other components of the delivery apparatus 100. The valve storage assembly 500 can include a nose cone cap 506 and a storage tube assembly 508. In at least certain implementations, the nose cone cap 506 is releasably secured to the storage tube assembly 508, such as through the use of slots and mating locking tabs, as described above. The nose cone 122 is at least partially disposed inside the nose cone cap 506, and the elongated shaft 120 of the nose cone catheter 118 extends proximally through the storage tube assembly 508.

A stylet 514 can be inserted into the nose cone cap 506 through an opening in the distal end of the nose cone cap 506. The stylet 514 can include a loop 516 at its distal end, a distal straight portion 518, a curved portion 520, and a proximal straight portion 522. The curved portion 520 can include at least one bend. Although the stylet 514 is shown with distal 518 and proximal 522 straight portions, in further implementations, the distal 518, proximal 522, or both distal 518 and proximal 522 straight portions are omitted from the stylet 514. That is, the curved portion 520 may be extended to take the place of the distal 518 or proximal 522 straight portions.

The incorporation of a bend in the curved portion 520 helps engage the stylet 514 with the lumen of the component in which the curved portion is located, such as to reduce undesired axial movement of the nose cone catheter 118. The effective width or diameter of the curved portion 520 is slightly greater than the inner diameter of the lumen through which it extends to create an interference fit between the lumen and the curved portion. Although the curved portion 520 is shown as located within the nose cone 122, the curved portion 520 could be located in a different component, or in additional components, such as in order to provide a desired degree of resistance to proximal axial movement of the nose cone catheter 118. For example, the curved section 520 can extend into the lumen of shaft 120. Similarly, parameters such as the number of bends in the curved portion, the width of the bends (and thus the effective diameter of the stylet in the curved portion), the degree of curvature of the bends, and the relative lengths of the distal 518 and proximal 522 straight portions can be adjusted to provide a desired degree of resistance. Generally, wider bends, sharper curvatures, and longer curved portions 520 will produce increased resistance to removal of the stylet 514 from the lumen through which it is inserted. In particular implementations, the amplitude or width of the bends in the curved portion 520, creates an effective diameter in the curved portion that is between about 5% and about 50% larger than the lumen through which the curved portion extends, such as between about 10% and about 40% larger, or between about 10% and about 30% larger.

FIGS. 38A and 38B illustrate an alternative implementation 600 of a valve-retaining mechanism. The valve-retaining mechanism 600 can be generally configured as described with reference to FIGS. 8B, 12, 19, and 20, for example. However, compared with the previously described valve-retaining mechanism 114, in FIGS. 38A and 38B, the prongs 606 of an inner fork (not shown in FIGS. 38A and 38B, but analogous to the inner fork 132 of FIG. 17) incorporate a bend 614. The bend 614 causes the distal end portions of the prongs 606 to be directed radially inwardly towards the shaft 120.

With reference to FIG. 38B, when the prosthetic valve 10 is secured to the retaining mechanism, the proximal ends of the retaining arms 30 of the frame 12 pass through the openings 140 in the distal ends of the prongs 134 of the outer fork 130, the prongs 606 extend adjacent the prongs 134 and then pass distally through the openings 32 of the retaining arms 30 of the frame 12 and then bend radially inwardly. Thus, where the retaining arms 30 pass through the openings 140, the prongs 606 are biased between the proximal ends of the retaining arms 30 and the portion of the prongs 134 of the outer fork 130 adjacent the proximal ends of the apertures 140.

It should be appreciated that incorporating the bends 614 into the prongs 606 helps maintain the relative positions of the prongs 606, prongs 134, and retaining arms 30 when then valve-retaining mechanism 600 is in the locked configuration, helping to prevent or reduce axial movement of these components. Because the prongs 606, the inner fork 132, and the nose cone 122 are coupled to the shaft 120 of the nose-cone catheter 118, this resistance to axial movement also helps maintain the position of the nose cone 122 relative to the distal end of the frame 12 and the other components of the delivery apparatus.

The angle of the bends 614 is typically selected to provide a desired degree of resistance to axial movement of the prongs 136 relative to the apertures 32 and the outer fork 130. Sharper bends 614 may help secure the valve-retaining mechanism 600 in the locked configuration. However, it also can result in a user having to apply a greater force to the inner fork 132 when the user desires to remove the prongs 606 from engagement with the apertures 32, causing the frame 12 to be released from the prongs 134 of the outer fork 130.

The bends 614 can be formed in the prongs 606 using any suitable method. In one implementation, the prongs 606 may be cut, such as by laser cutting, to incorporate the desired bend 614 at the appropriate location. In another implementation, the prongs 606 are bent, such as about a transverse axis, for example, an axis parallel to the width of the prongs 606, or an axis normal to the width. In a particular example, the prongs 606 are constructed from a shape memory material, such as nitanol. In such examples, the bends 614 can be formed in the desired shape by heat-setting the prongs 606.

In specific examples, the curve radius is between about 0.025 inches to about 0.75 inches, such as between about 0.05 inches and about 0.5 inches, or between about 0.1 inches and about 0.5 inches. In further examples, the distance between the axis of the unbent portion of the prongs 136, and the infection point at the apex of the bend is between about 75% and 400% of the width of the prong 606, such as being between about the width of the prong 606 and about three times the width of the prong 606.

The distance over which the bend 614 occurs can also affect the resistance provided by the bend 614. For example, for an equivalent bend severity (such as the distance between the axis of the prong 606 and the inflection point at the apex of the bend 614), a bend 614 occurring over a shorter distance will typically create more resistance than a bend of equivalent severity occurring over a longer distance. In a particular example, the bend 614 occurs over a distance of between about 5% and about 75% of the length of the prong 606, such as between about 10% and about 60%, or between about 20% and about 50%.

The bend 614 may also have different shapes. In some cases the, bend 614 has linear sides, such as being triangular or square. In other cases, the sides of the bend 614 are arcuate, such as having a parabolic shape. Typically, bends 614 with arcuate sides provide less resistance to movement of the prongs 134 and the apertures 32 than bends 614 with linear sides.

General Considerations

For purposes of this description, certain aspects, advantages, and novel features of the embodiments of this disclosure are described herein. The disclosed methods, devices, and systems should not be construed as limiting in any way. Instead, the present disclosure is directed toward all novel and nonobvious features and aspects of the various disclosed embodiments, alone and in various combinations and sub-combinations with one another. The methods, devices, and systems are not limited to any specific aspect or feature or combination thereof, nor do the disclosed embodiments require that any one or more specific advantages be present or problems be solved.

Features, integers, characteristics, compounds, chemical moieties, or groups described in conjunction with a particular aspect, embodiment, or example of the invention are to be understood to be applicable to any other aspect, embodiment, or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C" or "A, B and C."

As used herein, the term "coupled" generally means physically coupled or linked and does not exclude the presence of intermediate elements between the coupled items absent specific contrary language.

In view of the many possible embodiments to which the principles of the disclosed invention may be applied, it should be recognized that the illustrated embodiments are only preferred examples of the invention and should not be taken as limiting the scope of the invention. Accordingly, the scope of the invention is defined by the following claims. We therefore claim as our invention all that comes within the scope and spirit of these claims.

We claim:

1. A prosthetic valve delivery device, comprising:
a storage tube, the storage tube comprising a housing defining an internal chamber configured to receive a prosthetic valve, the storage tube further defining a first locking member; and
a nose cone cap, the nose cone cap defining an internal chamber comprising an enclosed distal end and an open proximal end, the open proximal end configured to receive a nose cone such that a distal end of the nose cone is proximate the enclosed distal end of the internal chamber and a proximal end of the nose cone is proximate the open proximal end of the internal chamber, the nose cone cap further defining a second locking member selectively couplable to the first locking member.

2. The prosthetic valve delivery device of claim 1, wherein the first locking member comprises at least one tab and the second locking member comprising at least one slot configured to receive the at least one tab so as to secure the nose cone cap to the storage tube.

3. The prosthetic valve delivery device of claim 1, wherein the nose cone cap comprises a pair of axially extending arms and the second locking member is formed on an arm of the pair of axially extending arms.

4. The prosthetic valve delivery device of claim 1, wherein the nose cone cap comprises a plurality of axial fins extending radially into the internal chamber of the nose cone cap.

5. The prosthetic valve delivery device of claim 4, wherein the plurality of axial fins define an inner bore configured to receive a stylet.

6. The prosthetic valve delivery device of claim 4, wherein the plurality of axial fins taper towards the distal end of the internal chamber of the nose cone cap.

7. The prosthetic valve delivery device of claim 1, wherein the housing comprises an aperture formed along a radial surface of the housing and configured to receive a retaining tab.

8. The prosthetic valve delivery device of claim 1, wherein the housing comprises proximal and distal portions that are selectively couplable.

9. The prosthetic valve delivery device of claim 8, wherein a proximal end of the distal portion defines a slot, and the proximal portion defines a locking tab configured to be received within the slot, wherein when the locking tab is received within the slot the proximal and distal portions of the housing are secured to one another.

10. A prosthetic valve delivery device, comprising:
a storage tube, the storage tube comprising a housing defining an internal chamber configured to receive a prosthetic valve, the storage tube further defining a first locking means for securing the storage tube; and
a nose cone cap, the nose cone cap defining an internal chamber comprising an enclosed distal end and an open proximal end, the open proximal end configured to receive a nose cone such that a distal end of the nose cone is proximate the enclosed distal end of the internal chamber and a proximal end of the nose cone is proximate the open proximal end of the internal chamber, the nose cone cap further defining a second locking means for securing the nose cone cap to the first locking means of the storage tube.

11. The prosthetic valve delivery device of claim 10, wherein the nose cone cap comprises a plurality of axial fins extending radially into the internal chamber of the nose cone cap.

12. The prosthetic valve delivery device of claim 11, wherein the plurality of axial fins define an inner bore configured to receive a stylet.

13. The prosthetic valve delivery device of claim 11, wherein the plurality of axial fins taper towards the distal end of the internal chamber of the nose cone cap.

14. The prosthetic valve delivery device of claim 10, wherein the housing comprises proximal and distal portions that are selectively couplable.

15. The prosthetic valve delivery device of claim 10, wherein a proximal end of the distal portion defines a slot, and the proximal portion defines a locking tab configured to be received within the slot, wherein when the locking tab is received within the slot the proximal and distal portions of the housing are secured to one another.

16. A prosthetic valve delivery device, comprising:
a storage tube, the storage tube comprising a housing defining an internal chamber configured to receive a prosthetic valve; and
a nose cone cap, the nose cone cap defining an internal chamber comprising an enclosed distal end and an open proximal end, the open proximal end configured to receive a nose cone such that a distal end of the nose cone is proximate the enclosed distal end of the internal chamber and a proximal end of the nose cone is proximate the open proximal end of the internal chamber, wherein the nose cone cap is releasably secured to the storage tube.

17. The prosthetic valve delivery device of claim 16, wherein the nose cone cap comprises a plurality of axial fins extending radially into the internal chamber of the nose cone cap.

18. The prosthetic valve delivery device of claim 17, wherein the plurality of axial fins taper towards the distal end of the internal chamber of the nose cone cap.

19. The prosthetic valve delivery device of claim 16, wherein the storage tube comprises at least one tab and the nose cone cap comprises at least one slot configured to receive the at least one tab so as to secure the nose cone cap to the storage tube.

20. The prosthetic valve delivery device of claim 19, wherein the nose cone cap comprises a pair of axially extending arms and the at least one slot is formed on an arm of the pair of axially extending arms.

* * * * *